(12) United States Patent
Carlson et al.

(10) Patent No.: US 9,185,087 B2
(45) Date of Patent: Nov. 10, 2015

(54) MEDICAL DEVICE COMMUNICATION USING ENCRYPTION BASED ON CORRELATED MOTION

(71) Applicant: Medtronic, Inc., Minneapolis, MN (US)

(72) Inventors: Timmothy S. Carlson, Fridley, MN (US); Duane L. Bourget, Albertville, MN (US)

(73) Assignee: Medtronic, Inc., Minneapolis, MN (US)

( * ) Notice: Subject to any disclaimer, the term of this patent is extended or adjusted under 35 U.S.C. 154(b) by 78 days.

(21) Appl. No.: 14/062,223

(22) Filed: Oct. 24, 2013

(65) Prior Publication Data

US 2015/0117645 A1    Apr. 30, 2015

(51) Int. Cl.
| | |
|---|---|
| *H04L 9/00* | (2006.01) |
| *H04L 9/32* | (2006.01) |
| *H04L 29/06* | (2006.01) |
| *H04W 12/04* | (2009.01) |
| *A61N 1/372* | (2006.01) |
| *H04L 9/08* | (2006.01) |

(52) U.S. Cl.
CPC ........ *H04L 63/0435* (2013.01); *A61N 1/37252* (2013.01); *H04L 9/0838* (2013.01); *H04L 9/0872* (2013.01); *H04L 63/068* (2013.01); *H04W 12/04* (2013.01); *H04L 2209/805* (2013.01); *H04L 2209/88* (2013.01)

(58) Field of Classification Search
CPC ......... H04L 9/12; H04L 9/08; H04L 63/0869; H04L 63/0435; H04L 9/0838; H04L 9/0872; H04L 63/068; H04W 12/04; H04W 12/06; H04W 12/08; G06F 21/123; A61N 1/3962; A61N 1/37252

USPC ........... 380/44, 255, 262, 270; 713/168–169, 713/189, 193; 607/57, 60
See application file for complete search history.

(56) References Cited

U.S. PATENT DOCUMENTS

| | | | |
|---|---|---|---|
| 6,558,321 B1 * | 5/2003 | Burd et al. ................... | 600/300 |
| 6,804,558 B2 | 10/2004 | Haller et al. | |
| 7,027,872 B2 | 4/2006 | Thompson | |

(Continued)

FOREIGN PATENT DOCUMENTS

WO    2008051983 A2    5/2008

OTHER PUBLICATIONS

Halperin, et al., "Security and Privacy for Implantabl Medical Devices," Pervasive Computing, Jan.-Mar. 2008, pp. 30-39.

(Continued)

*Primary Examiner* — Hosuk Song
(74) *Attorney, Agent, or Firm* — Shumaker & Sieffert, P.A.

(57) ABSTRACT

Devices, systems, and techniques for generating an encryption key using detected motion from a device. In one example, a method may include receiving movement information indicative of motion detected by a first device during a period of time in which the first device and a second device were bumped together, determining a set of values that represent at least one characteristic of the movement information, and generating, based on the set of values, an encryption key for at least one of encrypting and decrypting data communicated between the first device and the second device. In some examples, the first device may include a sensor configured to detect each time the first device is bumped with the second device during the period of time. The first and second devices may be an implantable medical device and a programmer for the implantable medical device.

38 Claims, 9 Drawing Sheets

(56) References Cited

U.S. PATENT DOCUMENTS

| | | | |
|---|---|---|---|
| 7,039,810 B1 | 5/2006 | Nichols | |
| 7,155,290 B2 | 12/2006 | Von Arx et al. | |
| 7,475,245 B1 | 1/2009 | Healy et al. | |
| 7,907,901 B1 | 3/2011 | Kahn et al. | |
| 7,978,062 B2 * | 7/2011 | LaLonde et al. | 340/539.11 |
| 8,126,728 B2 | 2/2012 | Dicks et al. | |
| 8,126,732 B2 | 2/2012 | Dicks et al. | |
| 8,126,733 B2 | 2/2012 | Dicks et al. | |
| 8,126,734 B2 | 2/2012 | Dicks et al. | |
| 8,214,043 B2 * | 7/2012 | Matos | 607/30 |
| 8,245,583 B2 | 8/2012 | Stein | |
| 8,301,110 B2 | 10/2012 | Roberts et al. | |
| 8,327,139 B2 | 12/2012 | Healy et al. | |
| 8,331,563 B2 | 12/2012 | Healy et al. | |
| 8,707,040 B2 * | 4/2014 | Andersen | 713/169 |
| 2007/0188323 A1 | 8/2007 | Sinclair et al. | |
| 2008/0019514 A1 | 1/2008 | Stromberg et al. | |
| 2009/0082834 A1 | 3/2009 | Kalpin et al. | |
| 2009/0270949 A1 | 10/2009 | Kalpin et al. | |
| 2010/0199092 A1 | 8/2010 | Andrus et al. | |
| 2010/0331738 A1 | 12/2010 | Stein et al. | |
| 2011/0160616 A1 | 6/2011 | Stein et al. | |
| 2011/0179405 A1 | 7/2011 | Dicks et al. | |
| 2011/0319755 A1 | 12/2011 | Stein et al. | |
| 2012/0197347 A1 | 8/2012 | Olson et al. | |
| 2012/0197348 A1 | 8/2012 | Bornhoft et al. | |
| 2012/0197351 A1 | 8/2012 | Olson et al. | |
| 2013/0069780 A1 | 3/2013 | Tran | |
| 2014/0055284 A1 * | 2/2014 | Tran et al. | 340/870.07 |

OTHER PUBLICATIONS

Moller, et al., "Prototype of a secure wireless patient monitoring system for the medical community," Sensors and Actuators, Jan. 2012, pp. 54-65.

Xu, et al., "IMDGuard: Securing Implantable Medical Devices with the External Wearable Guardian," Department of Computer Science, The College of William and Mary, Apr. 2011, 9 pp.

International Search Report and Written Opinion from Counterpart International Patent Application Number PCT/US2014/055544, mailed Jan. 23, 2015, 9 pp.

* cited by examiner

MEDICAL DEVICE COMMUNICATION USING ENCRYPTION BASED ON CORRELATED MOTION

TECHNICAL FIELD

The disclosure relates to medical device communication and, more particularly, encrypting communications to or from medical devices.

BACKGROUND

A computing device may be configured to transmit communications to, and receive communications from, other computing devices. These communications may include data or any information that is transmitted between devices either wirelessly of via a wired connection. Communications that are public or otherwise do not include sensitive information may be unsecured. Communications that are intended to be private to two or more devices may be encrypted such that the information contained therein is not readily available to unauthorized devices.

In some examples, communications between an external device (e.g., a medical device programmer) and an implantable medical device (e.g., a pacemaker, a defibrillator, a neurostimulator, or a drug pump) may be encrypted to secure sensitive information such as collected patient data or programming instructions that at least partially define the operation of an implantable medical device. Secure communication involving medical devices may involve an encryption scheme known to both the external device and the implantable medical device. For example, both the external device and the implantable medical device may utilize a stored encryption key to encrypt and/or decrypt some or all information transmitted between the devices.

SUMMARY

In general, the disclosure is directed to devices, systems, and techniques for generating encryption keys for medical device communication using detected motion. Prior to secure communication between two devices (e.g., a medical device programmer and an implantable medical device), the two devices may each generate an encryption key. For example, the programmer may deliver a prompt to a user (e.g., a clinician or a patient) that instructs the user to "bump" or "tap" the programmer against the implantable medical device (IMD), or against patient tissue a location over the IMD, one or more times. Each of the programmer and IMD can then detect the resulting motion from each bump with respective sensors. The detected motion at each device may be correlated with the motion at the other device. In other words, acceleration changes, velocities, number of bumps, durations between each bump, or other characteristics of the detected motion will occur at approximately the same time, and possibly with similar magnitude.

Using the detected motion, each device can generate an encryption key. For example, each of the devices, e.g., the programmer and IMD, may determine a set of values (e.g., one or more values) indicative of one or more characteristics of the detected motion, such that the set of values are used to generate the encryption key. Since the determined set of values should be identical, even though the accelerometer data from each device may be similar but not identical, the encryption key independently generated from each device may also match such that the keys can be used to encrypt and decrypt communications transmitted between the devices. In other examples, each device may generate a respective encryption key and decryption key for communications with the other device.

In one example, the disclosure is directed to a method that includes receiving movement information indicative of motion detected by a first device during a period of time in which the first device and a second device were bumped together, determining a set of values that represent at least one characteristic of the movement information, and generating, by one or more processors and based on the set of values, an encryption key for at least one of encrypting and decrypting data communicated between the first device and the second device.

In another example, the disclosure is directed to a system that includes one or more processors configured to receive movement information indicative of motion detected by a first device during a period of time in which the first device and a second device were bumped together, determine a set of values that represent at least one characteristic of the movement information, and generate, based on the set of values, an encryption key for at least one of encrypting and decrypting data communicated between the first device and the second device.

In another example, the disclosure is directed to a computer-readable storage medium that includes instructions that cause one or more processors to receive movement information indicative of motion detected by a first device during a period of time in which the first device and a second device were bumped together, determine a set of values that represent at least one characteristic of the movement information, and generate, based on the set of values, an encryption key for at least one of encrypting and decrypting data communicated between the first device and the second device.

In one example, the disclosure is directed to a system that includes means for receiving movement information indicative of motion detected by a first device during a period of time in which the first device and a second device were bumped together, means for determining a set of values that represent at least one characteristic of the movement information, and means for generating, based on the set of values, an encryption key for at least one of encrypting and decrypting data communicated between the first device and the second device.

The details of one or more example are set forth in the accompanying drawings and the description below. Other features, objects, and advantages will be apparent from the description and drawings, and from the claims.

DETAILED DESCRIPTION

Figure 1:
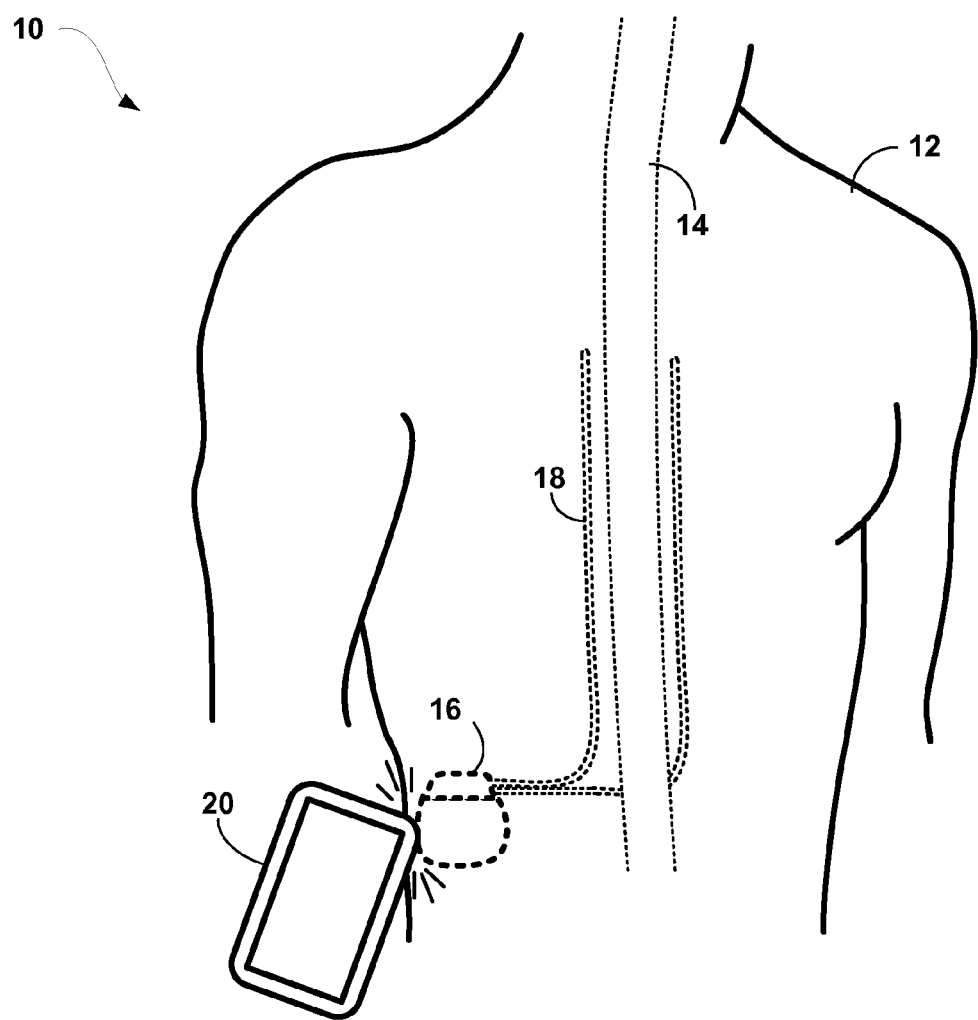
FIG. 1 is a conceptual diagram illustrating an example external programmer and an example implantable medical device configured to generate encryption keys based on correlated motion from one or more physical bumps with each other.

This disclosure is generally directed to devices, systems, and techniques for generating encryption keys using detected motion. Computing devices may be configured to transmit and/or receive communications with other computing devices. In the context of medical devices, an implantable medical device (IMD) may be implanted within a patient and still need to communicate with other computing devices such as external medical device programmers, external sensors, or any other such devices in order to receive adjustments to therapy parameters, operational instructions, or operational queries, and/or transmit sensed data from the patient. Without securing, or encrypting, this information that is communicated to or from the IMD, the IMD may become vulnerable to malicious actions by unauthorized users and/or sensitive data from the patient may be accessed by unauthorized users.

Typically, an IMD and external devices may be configured to encrypt the communications between these devices. This encryption may require the exchange of an encryption key or information for use in generation of an encryption key, such that the encryption key is then known both to the IMD and the one or more external devices with which the IMD will communicate. The encryption key may be transmitted in such a manner that is difficult for an unauthorized user to detect, e.g., using an "out-of-band" exchange where the encryption key is transmitted via a medium different than the medium in which communication will be secured using the encryption key. Example methods for exchanging the encryption keys include pre-sharing the encryption key prior to implanting the IMD, sharing the encryption key in a safe context (e.g., when the IMD and external device are located in an uncompromised location or area), and sharing the encryption key using a short-range wireless radio frequency (RF) or inductive communication link that limits the range of the transmission signals. Each of these methods may have respective limitations such as difficulty changing the encryption key should it become compromised, possible interception of the transmitted encryption key by an unauthenticated user, and the need for additional components and power usage otherwise unnecessary to the operation of the IMD and/or external devices.

As described herein, devices may be configured to generate an encryption key using detected motion instead of receiving the encryption key from another device. Prior to secure communication between two devices (e.g., a medical device programmer and an IMD), the two devices may each generate an encryption key. For example, the programmer may deliver a prompt to a user (e.g., a clinician or a patient) that instructs the user to "bump" or "tap" the programmer against the implantable medical device (IMD) one or more times. The IMD may be implanted subcutaneously or at another location from which the IMD can detect contact of the programmer with the patient. Accordingly, the programmer may be bumped against patient tissue between the programmer and the IMD, such mechanical force of the bump is at least partially transmitted to the IMD. Each of the programmer and IMD can then detect the resulting motion from each bump with respective sensors (e.g., one or more accelerometers). The detected motion at each device is thus correlated with the motion at the other device. In particular, the motion detected by the device that transmitted the motion and the device that received the motion will be correlated in several respects. For example, changes, velocities, number of bumps, durations between each bump, or other characteristics of the detected motion will occur at approximately the same time and with similar magnitude, whether detected by the programmer or detected by the IMD.

Using movement information received from a respective sensor and indicative of the detected motion, each device may be configured to generate a respective encryption key. For example, each of the devices, e.g., the programmer and IMD, may determine a set of values indicative of one or more characteristics of the movement information, where the set of values are used to generate the encryption key. Since the set of values determined by the IMD and the programmer should be identical or nearly identical, each device should independently generate matching, or identical, encryption keys. In other words, the two encryption keys may be described as a shared encryption key. Each device can then use the respective generated encryption key to encrypt and/or decrypt communications transmitted between the devices. In other examples, each device may generate respective keys specific to encryption or decryption. By generating encryption keys using correlation motion from physically bumping two devices together, e.g., directly in contact with one another or across a patient tissue interface, encryption keys do not need to be transmitted to or from any device, encryption keys can be regenerated if compromised, and no additional communication components are needed to send or receive encryption keys out-of-band. In this manner, two devices may be bumped together prior to implantation and/or post-implantation.

The examples described herein for generating encryption keys are generally related to IMDs and external medical device programmers configured to control each IMD. However, other devices may also utilize detected motion from correlated "bumps" to generate encryption keys. For example, such devices may include external medical devices, wearable computing devices, or any other computing devices that may utilize secured communications.

FIG. 1 is a conceptual diagram illustrating an example external programmer 20 and an example IMD 16 configured to generate encryption keys based on correlated motion from one or more physical bumps with each other, e.g., as transmitted across the patient tissue between the external programmer and the IMD. System 10 may be configured to include secure communication between programmer 20 and IMD 16 using shared encryption keys generated independently by programmer 20 and IMD 16. The encryption keys may be generated by using characteristics of the motion detected when programmer 20 is bumped into IMD 16.

As shown in FIG. 1, system 10 includes an IMD 16 and external programmer 20 shown in conjunction with a patient 12, who is ordinarily a human patient. In the example of FIG. 1, IMD 16 is an implantable electrical stimulator that delivers neurostimulation therapy to patient 12, e.g., for relief of chronic pain or other symptoms such as abnormal movements. Generally IMD 16 may be a chronic electrical stimulator (or a device that chronically delivers a pharmacological agent to a patient (e.g., a drug pump device)) that remains implanted within patient 12 for weeks, months, or even years. In the example of FIG. 1, IMD 16 and leads 18 may be directed to delivering SCS therapy. In other examples, IMD 16 may be a temporary, or trial, stimulator used to screen or evaluate the efficacy of electrical stimulation or drug delivery for chronic therapy. IMD 16 may be implanted in a subcutaneous tissue pocket, within one or more layers of muscle, or other internal location. IMD 16 may be coupled to leads 18A and 18B (collectively "leads 18"). Although IMD 16 may be implanted beneath tissue of patient 12, IMD 16 and programmer 20 may still detect one or more physical impacts from bumping programmer 20 into IMD 16, e.g., across patient tissue between the IMD and programmer.

IMD 16 may be configured to generate and deliver electrical stimulation energy, which may be constant current or constant voltage based pulses, for example, that is delivered from IMD 16 to one or more targeted locations within patient 12 via one or more electrodes (not shown) of leads 18. The therapy parameters for a program that controls delivery of stimulation energy by IMD 16 may include information identifying which electrodes have been selected for delivery of stimulation according to a stimulation program, the combination of the selected electrodes, and the polarities of the selected electrodes, i.e., the electrode configuration for the program, and voltage or current amplitude, pulse frequency (or pulse rate), pulse shape, and pulse width of stimulation delivered by the electrodes. Electrical stimulation may be delivered in the form of stimulation pulses or continuous waveforms, for example. Programmer 20 may be configured to transmit these programs, therapy parameters, and/or adjustments to therapy parameters to IMD 16.

In the example of FIG. 1, leads 18 are disposed within patient 12, e.g., implanted within patient 12. Leads 18 tunnel through tissue of patient 12 from along spinal cord 14 to a subcutaneous tissue pocket or other internal location where IMD 16 is disposed. Although leads 18 may include two leads, leads 18 may include a single lead that bifurcates into both of leads 18, one or more lead extensions, or other segments that may aid in implantation or positioning of leads 18. In other examples, IMD 16 may be electrically coupled to a single lead or three or more leads. In addition, a proximal ends of each of leads 18 may include a connector (not shown) that electrically couples to a header (not shown) of IMD 16. Each of leads 18 coupled to IMD 16 may be directed to similar or different target tissue sites. For example, the multiple leads 18 may be disposed along spinal cord 14 or leads 18 may be directed to spinal cord 14 and/or other locations within patient 12. Each of leads 18 may carry one or more electrodes that are placed adjacent to the target tissue, e.g., spinal cord 14 for spinal cord stimulation (SCS) therapy.

IMD 16 is configured to deliver electrical stimulation therapy to patient 12 via selected combinations of electrodes carried by leads 18. The target tissue for the electrical stimulation therapy may be any tissue affected by electrical stimulation energy, which may be in the form of electrical stimulation pulses or waveforms. In some examples, the target tissue includes nerves, smooth muscle, and skeletal muscle. In the example illustrated by FIG. 1, the target tissue for electrical stimulation delivered via leads 18 is tissue proximate spinal cord 14 (e.g., one or more target locations of the dorsal columns or one or more dorsal roots that branch from spinal cord 14). Leads 18 may be introduced into spinal cord 14 via any suitable region, such as the thoracic, cervical or lumbar regions. Stimulation of dorsal columns, dorsal roots, and/or peripheral nerves (e.g., afferent nerves) may, for example, prevent pain signals from traveling through spinal cord 18 and to the brain of the patient. Patient 12 may perceive the interruption of pain signals as a reduction in pain and, therefore, efficacious therapy results. For treatment of other disorders, leads 18 may be introduced at any exterior location of patient 12.

Although leads 18 are described as generally delivering or transmitting electrical stimulation signals, leads 18 may additionally transmit electrical signals from patient 12 to IMD 16 for monitoring. For example, IMD 16 may utilize detected nerve impulses to diagnose the condition of patient 12 or adjust the delivered stimulation therapy. Leads 18 may thus transmit electrical signals to and from patient 12.

IMD 16 may receive therapy parameters and other operational instructions from external programmer 20. A user, such as a clinician or patient 12, may interact with a user interface of an external programmer 20 to program IMD 16. Programming of IMD 16 may refer generally to the generation and transfer of commands, programs, therapy parameter values, or other information to control the operation of IMD 16. In this manner, IMD 16 may receive the transferred commands and programs from programmer 20 to control stimulation therapy. For example, external programmer 20 may transmit programs, parameter adjustments, program selections, group selections, user input, or other information to control the operation of IMD 16, e.g., by wireless telemetry or wired connection. As described herein, transmission of any data from programmer 20 to IMD 16 may include encrypted data to secure the operation of IMD 16.

Programmer 20 may be a clinician programmer that the clinician uses to communicate with IMD 16 and program one or more therapy programs for IMD 16. Alternatively, programmer 20 may be a patient programmer that allows patient 12 to select programs and/or view and modify therapy parameters. The clinician programmer may include more programming features than the patient programmer. In other words, more complex or sensitive tasks may only be allowed by the clinician programmer to prevent an untrained patient from making undesirable changes to IMD 16.

IMD 16 may be constructed of any polymer, metal, or composite material sufficient to house the components of IMD 16 (e.g., components illustrated in FIG. 2) within patient 12. In this example, IMD 16 may be constructed with a biocompatible housing, such as titanium or stainless steel, or a polymeric material such as silicone or polyurethane, and surgically implanted at a site in patient 12 near the pelvis, abdomen, or buttocks. The housing of IMD 16 may be configured to provide a hermetic seal for components, such as a rechargeable power source. In addition, the housing of IMD 16 may be selected of a material that facilitates receiving energy to charge a rechargeable power source.

Although IMD 16 is generally described in FIG. 1, techniques of this disclosure may also be applicable to external or partially external medical device in other examples. For example, IMD 16 may instead be configured as an external medical device coupled to one or more percutaneous medical leads. The external medical device may be a chronic, temporary, or trial electrical stimulator. In addition, an external electrical stimulator may be used in addition to one or more IMDs 16 to deliver electrical stimulation described herein.

IMD 16 may also be configured to deliver therapy other than SCS. For example, system 10 and IMD 16 may be configured to deliver peripheral nerve field stimulation (PNFS), occipital nerve stimulation, sacral nerve stimulation (SNS), pelvic floor stimulation, deep brain stimulation (DBS) or any other electrical stimulation therapy. Additionally or alternatively, IMD 16 may be configured to deliver drug therapy or any other type of therapy. In some examples, IMD 16 may coordinate therapy with one or more additional IMDs implanted within patient 12 or medical devices external from patient 12. These IMDs may also transmit data between each other subject to encryption strategies described herein.

As described herein, information may be transmitted between external programmer 20 and IMD 16. Therefore, IMD 16 and programmer 20 may communicate via wireless communication. Examples of communication techniques may include, for example, radiofrequency (RF) telemetry and inductive coupling, but other techniques are also contemplated. In some examples, programmer 20 may include a communication head that may be placed proximate to the patient's body near the IMD 16 implant site in order to improve the quality of communication between IMD 16 and programmer 20. Communication between programmer 20 and IMD 16 may occur during power transmission or separate from power transmission.

However, communications (e.g., information or data) transmitted between programmer 20 and IMD 16 may be encrypted to secure the communications from unauthenticated users and prevent programmer 20 and IMD 16 from becoming compromised. As described herein, programmer 20 and IMD 16 may generate their own encryption keys using detected motion resulting from programmer 20 and IMD 16 being "bumped" or "tapped" together. Only authenticated programmers and IMDs may have matching protocols for generating the encryption keys to prevent any other unauthenticated device from generating a matching encryption key. In other words, unauthenticated devices may not have access to the encryption key generation protocols which are not transmitted between each authenticated device. This process may eliminate potential security breaches caused by transmission of shared encryption keys between devices and allow for new encryption keys to be generated when needed.

For example, a system (e.g., system 10, programmer 20, or IMD 16) may include one or more processors configured to receive movement information indicative of motion detected by programmer 20 during a period of time in which programmer 20 and IMD 16 were bumped together. Programmer 20 may then determine a set of values that represent at least one characteristic of the movement information. Based on the determined set of values, programmer 20 may independently generate an encryption key for at least one of encrypting and decrypting communication between programmer 20 and IMD 16. In addition, IMD 16 may perform similar steps in order to also independently generate an encryption key. Since both encryption keys are based on the movement information indicative of the motion detected by each device during the common bump session, the independently generated encryption keys may function in a manner similar to a shared encryption key.

Encryption keys may be generated as an initialization process for communication between programmer 20 and IMD 16. This initialization process may only occur once prior to the first secured communication between programmer 20 and IMD 16, periodically over time, or as needed to maintain security of the communications over time. As some examples, the initialization process for generating encryption keys may be performed after a predetermined time has elapsed since the previous initialization process, after a predetermined number of times programmer 20 and IMD 16 has communicated, after either programmer 20 or IMD 16 has communicated with a different device, upon request by a user, or in response to detecting that a currently used encryption key may have been compromised.

Programmer 20 and/or IMD 16 may start the initialization process in response to receiving user input request, receiving a request from the other device for information to be transmitted, or in response to detecting the other device, for example. For example, programmer 20 may be configured to receive a request to initiate communication between programmer 20 and IMD 16. In response to receiving the request, programmer 20 may then output, for display via a display device (e.g., a screen of programmer 20), a command instructing the user to perform a bump sequence between programmer 20 and IMD 16. The bump sequence may include one or more physical bumps of programmer 20 against IMD 16 (i.e., programmer 20 may contact the skin and other tissue between programmer 20 and IMD 16). In response to receiving movement information indicative of the bump sequence, programmer 20 may be configured to determine the set of values indicative of at least one characteristic of the movement information used to generate an encryption key.

As described here, the correlated motion from bumping programmer 20 and IMD 16 may require a user (e.g., a clinician or patient 12) to physically cause programmer 20 and IMD 16 to come in contact with each other (e.g., perform a "bump"). Of course, programmer 20 and IMD 16 will not actually touch each other because some tissue (e.g., skin and adipose tissue) still remains between programmer 20 and IMD 16. Therefore, a "bump" between programmer 20 and IMD 16 may occur when programmer 20 and IMD 16 compress the tissue between the devices, and transmits mechanical force of the bump to the IMD. Programmer 20 and/or IMD 16 may deliver a prompt to the user to perform one or more bumps. The prompt may be instructions presented on a display of programmer 20, an audible beep or verbal instructions delivered by programmer 20, a vibration or audible prompt from IMD 16, or any other type of prompt that can signal the user to start bumping programmer 20 against IMD 16. The prompt from programmer 20 may also provide details about the bump, such as a suggested number of bumps, strength of the bumps, duration for continued bumping of programmer 20 against IMD 16, or any other similar instructions. The time period during which bumps between programmer 20 and IMD 16 occur may be described as a "bump session."

Each of programmer 20 and IMD 16 may include one or more sensors configured to detect the motion of each bump and generate movement information indicative of each bump during the bump session. These sensors may include one or more accelerometers, gyroscopes, or any other components may generate a signal in response to detecting motion. The sensors may be activated in response to the beginning of each bump session or only data generated during the bump session may be stored. Each of the sensors may output movement information. In some examples, the movement information may include a calibration or scaling factor to account for dissipation of motion energy into the tissue surrounding IMD 16. The movement information may be in the form of one or more analog signals, digital signals, raw data, calibrated data, or any other information indicative of the detected motion. For example, the movement information may include detected motion that has been converted into a 1-axis magnitude that accounts for various orientations of programmer 20 and IMD 16.

Each bump session may be coordinated by one of the devices. For example, programmer 20 and IMD 16 may transmit unsecured communications indicating that the bump session is to begin. Each bump session may be started at a selected time or in response to a first detected bump. The bump session from which encryption keys are generated may be limited to a predetermined duration. For example, the time period of the bump session may be limited to a predetermined duration of time or a predetermined number of detected bumps. Alternatively, programmer 20 and IMD 16 may determine the end of each bump session by the lack of any detected motion after a predetermined period of time.

Figure 6:
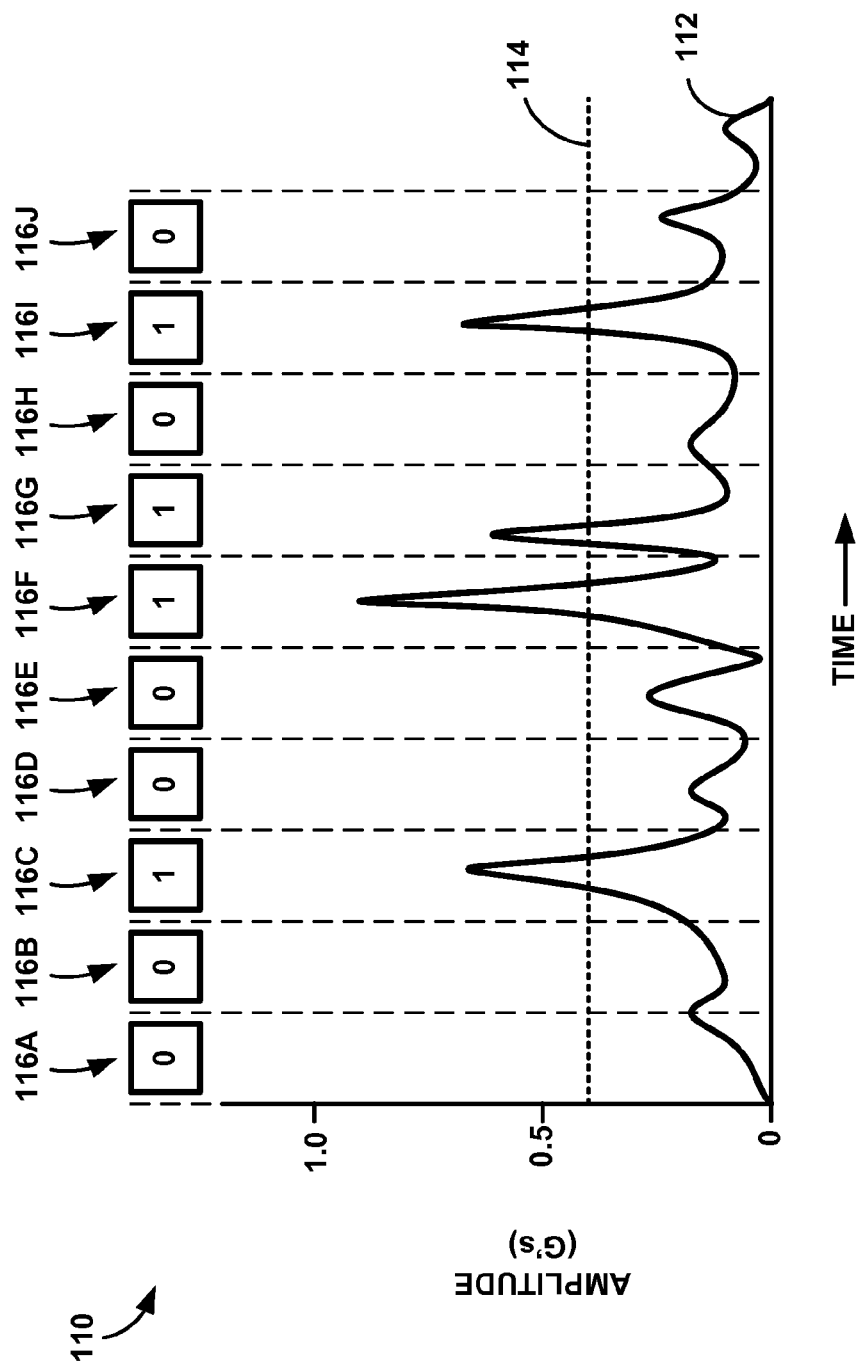
FIG. 6 is a graph illustrating the generation of an example encryption key from detected motion and a single amplitude threshold.

Programmer 20 and IMD 16 may receive the movement information indicative of the respective motion. In response to receiving the movement information, programmer 20 and IMD 16 may determine a set of values that represents one or more characteristics of the movement information. The characteristics of the movement information may include one or more amplitudes of the acceleration signal of the movement information. In other words, the set of values may be representative of the amplitudes of the acceleration of the device detected during the bump session. For example, programmer 20 and IMD 16 may determine the set of values by segmenting the bump session into a plurality of time slots and, for each of the plurality of time slots, compare an amplitude of the acceleration signal of the movement information to predetermined amplitude threshold (e.g., as shown in FIG. 6). Programmer 20 and IMD 16 may then assign a first value to each of the plurality of time slots in which the amplitude of the acceleration signal exceeds the amplitude threshold and assign a second value to each of the plurality of time slots in which the amplitude of the acceleration signal does not exceed the amplitude threshold. The first and second values may be any different values (e.g., a 1 and a 0) such that they represent supra-threshold and sub-threshold amplitudes for each time slot. Programmer 20 and IMD 16 may then be configured to order the first and second values according to a chronological sequence of the time slots to create the set of values. This determined set of values may then be used as the encryption keys or used to generate the encryption keys using an additional algorithm.

Figure 7:
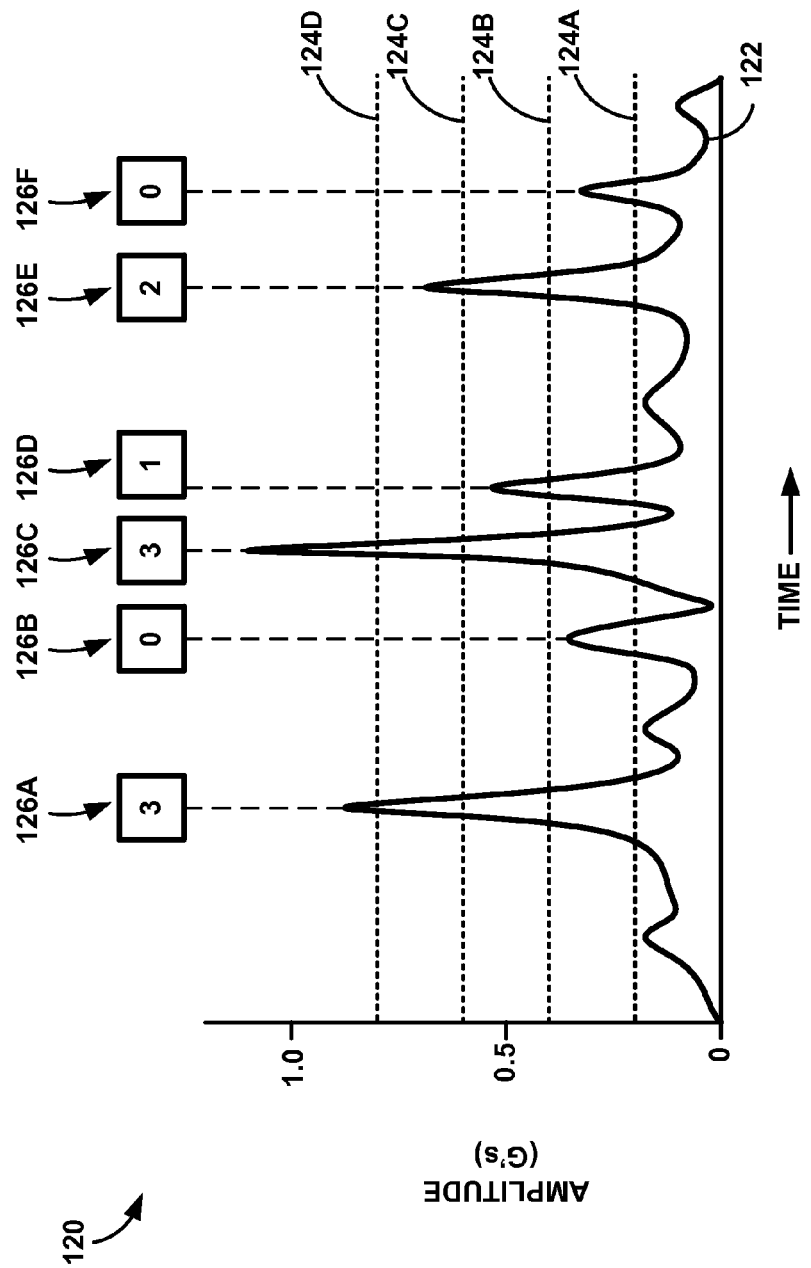
FIG. 7 is a graph illustrating the generation of an example encryption key from detected motion and multiple amplitude thresholds.

In another example, determining the set of values may include multiple amplitude thresholds as shown in FIG. 7. Programmer 20 and IMD 16 may compare an amplitude of the acceleration signal of the movement information to a plurality of different amplitude thresholds. Each of the plurality of different amplitude thresholds may correspond to a respective value that is used in the set of values. For each amplitude peak of the acceleration signal exceeding at least one of the plurality of different amplitude thresholds, programmer 20 and IMD 16 may assign, to the amplitude peak, the respective value corresponding to the highest amplitude threshold exceeded by the respective amplitude peak. Programmer 20 and IMD 16 may then order the assigned values according to the chronological occurrence of the respective amplitude peaks during the period of time to create the set of values. This determined set of values may then be used as the encryption keys or used to generate the encryption keys using an additional algorithm.

Figure 8:
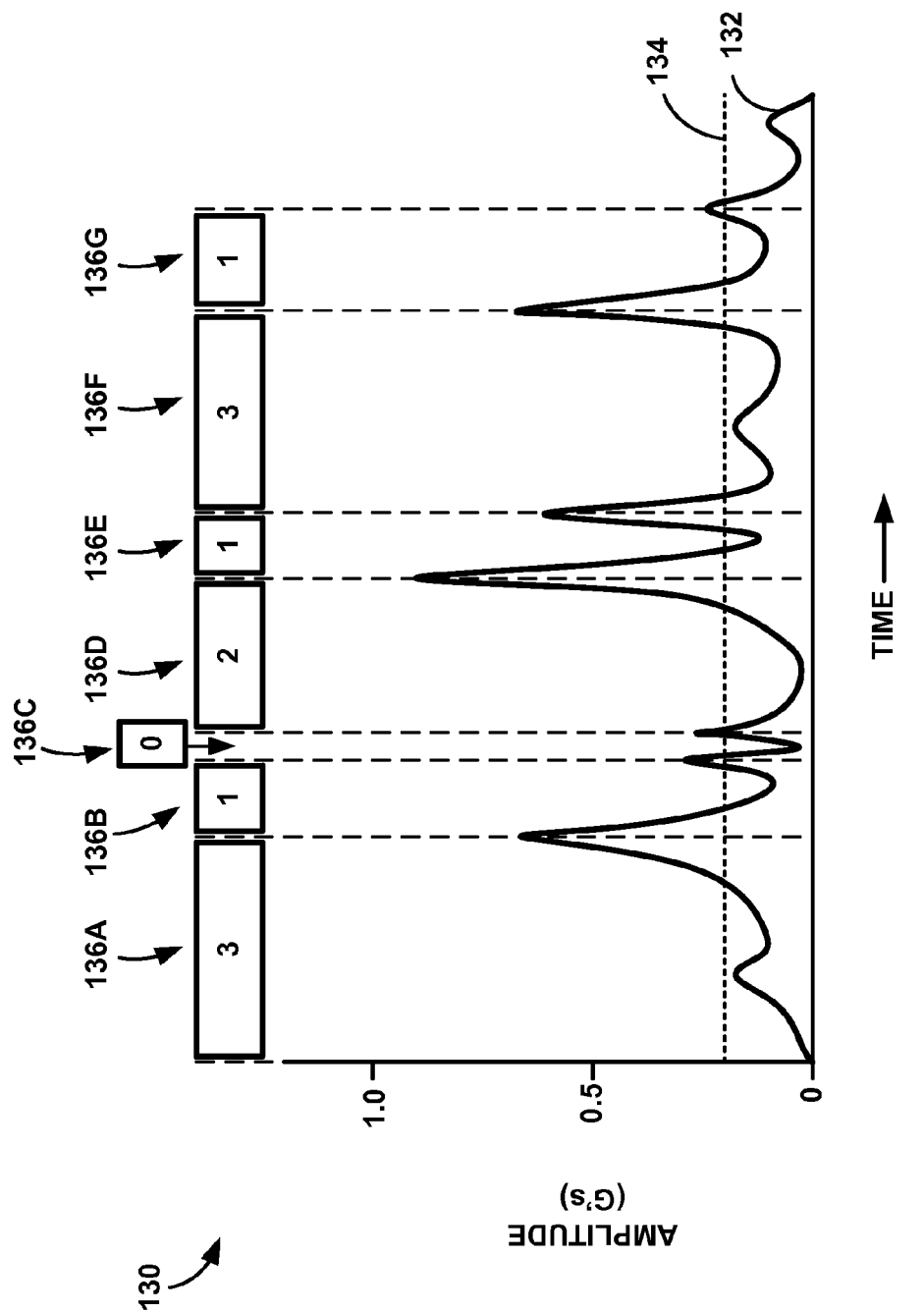
FIG. 8 is a graph illustrating the generation of an example encryption key from durations of time between supra-threshold amplitude peaks of detected motion.

The characteristics of the movement information may alternatively be one or more time periods between respective supra-threshold amplitude peaks of the acceleration signal of the movement information, as shown in FIG. 8. Programmer 20 and IMD 16 may determine the set of values by comparing the amplitude of the acceleration signal of the movement information to a predetermined amplitude threshold. For each pair of amplitude peaks of the acceleration signal exceeding the amplitude threshold, programmer 20 and IMD 20 may calculate a respective time duration between the pair of amplitude peaks. Programmer 20 and IMD 20 may then match each of the respective time durations to one of a plurality of duration ranges, wherein each of the plurality of duration ranges corresponds to a respective value. In other words, programmer 20 and IMD 16 may sort the calculated time durations into a predetermined number of ranges, or buckets, that essentially categorize the time durations. Programmer 20 and IMD 16 may then assign, based on the matching of the time durations to the ranges, the corresponding value of the matching duration range to the respective time durations and order the assigned values according to the chronological occurrence of the respective time durations during the period of time to create the set of values. This determined set of values may then be used as the encryption keys or used to generate the encryption keys using an additional algorithm.

In any example in which one or more thresholds are used to determine the set of values, the thresholds for one device may be different for another device. For example, the thresholds used by IMD 16 may be lower than the thresholds used by programmer 20. Since IMD 16 may be surrounded by skin, fat, and other tissue, the accelerations resulting from a bump with programmer 20 may be attenuated. Therefore, IMD 16 and programmer 20 may use thresholds that are different in order to determine an identical set of values for the identical encryption keys. In some examples, the thresholds may be patient-specific and based on a level of body fat of the patient, a depth of device implant, an implant orientation, a location of the implant, or any other such variables. These thresholds may be determined upon implant and incorporated as part of the instructions for determining the set of values.

In some examples, the thresholds may be determine from a calibration session between the devices (e.g., IMD 16 and programmer 20). For example, a user may be directed to provide a substantial single bump. Each device may calibrate the thresholds based on the detected amplitude of the single bump, such as a percentage or fraction of the bump amplitude. The calibration session may be separate from any bump session. Alternatively, the calibration may be performed by each device from the first bump detected in every bump session. The first bump may thus be a "calibration bump" used to set each of the thresholds. In another example, the calibration session may involve the generation and exchange of multiple calibration encrypted data sets. Each device may set the thresholds, generate an encryption key, use the encryption key to generate a calibration encrypted data set, and transmit the calibration encrypted data set to the other device. The receiving device may then attempt to decrypt the calibration encrypted data set to ensure that the encryption keys match. If the encryption keys do not match, each device may recalibrate the thresholds. This process may continue until each device has calibrated the thresholds such that reliably matching encryption keys can be generated by each device.

Other characteristics of the movement information may also, or alternatively, be used to determine the set of values. For example, the characteristic may include a frequency spectrum of the acceleration signal of the movement information. Programmer 20 and IMD 16 may perform a fast Fourier transform on the acceleration signal to determine the frequency spectrum of the acceleration signal. The frequency spectrum may then be used to identify one or more frequencies of greater power or otherwise select a set of values from the frequency spectrum. For example, the set of values may be generated from the number of frequencies having an amplitude above a threshold, the number of frequency amplitudes above threshold within each of a plurality of predetermined frequency ranges, the frequency ranges between frequency amplitudes above a threshold, or any other identifying features from the frequency spectrum. These and any other characteristics of the movement information may be used to generate the encryption key. In some examples, multiple characteristics of the movement information may be used to determine a more complex set of values and more robust encryption key.

After the set of values is determined from the movement information, programmer 20 and IMD 16 may generate the respective encryption keys independently from each other. However, each encryption key may be matching due to the correlated motion from the bumps of programmer 20 into IMD 16. In some examples, generation of the encryption key may be simply selection of the set of values. In other examples, the generation of the encryption key may include application of one or more additional algorithms to the set of values. For example, the additional algorithms may include multipliers, addition or subtraction, insertion of values before, in between, or after the set of values, or even the inclusion of data specific to one or more of the devices (e.g., a serial number or model number) and/or data specific to the patient (e.g., personal information or detected physiological data). In any case, the encryption key may be generated without transferring the encryption key to or from either of programmer 20 and IMD 16.

The instructions for determination of the set of values and/or generation of the encryption key may be stored in a memory of each of programmer 20 and IMD 16 at manufacture, prior to implantation, or as part of an implantation procedure. In some examples, determination of the set of values may be performed at a networked server. For example, IMD 16 may send the movement information to a networked server to perform the calculations without using power from the IMD to perform the task. The networked server may then transmit the set of values back to IMD 16. IMD 16 may then, in response to receiving the set of values, generate the encryption key using instructions previously stored in IMD 16 for using such values to generate the encryption key.

After the encryption keys are generated in each of programmer 20 and IMD 16, secure communications may commence. For example, programmer 20 may encrypt programming instructions for IMD 16 using the encryption key generated by the programmer and transmit the encrypted communications to IMD 16. IMD 16 may then use the matching encryption key generated by IMD to decrypt the instructions. Similarly, IMD 16 may send encrypted communications to programmer 20. Although FIG. 1 is directed to programmer 20 and IMD 16, any two or more computing devices may similarly be configured to detect correlated motion and generate encryption keys based on that motion to eliminate the need to transmit encryption keys to or from devices.

In some examples, errors may occur during the bump session such that the motion detected by each device (e.g., programmer 20 and IMD 16) may not be mirror images of each other. For example, one or both devices may come into contact with another object, the user may sneeze or move unexpectedly, the angle of contact may not effectively transmit the bump similarly, or any other anomaly can occur. If the encryption keys do not match, programmer 20 and IMD 16 may not transmit secure communications. If either of programmer 20 or IMD 16 detects that the encryption keys are not matched, such as identifying data that cannot be decrypted, the device may request another initiation procedure and bump session to try and correctly generate the encryption keys another time.

Figure 2:
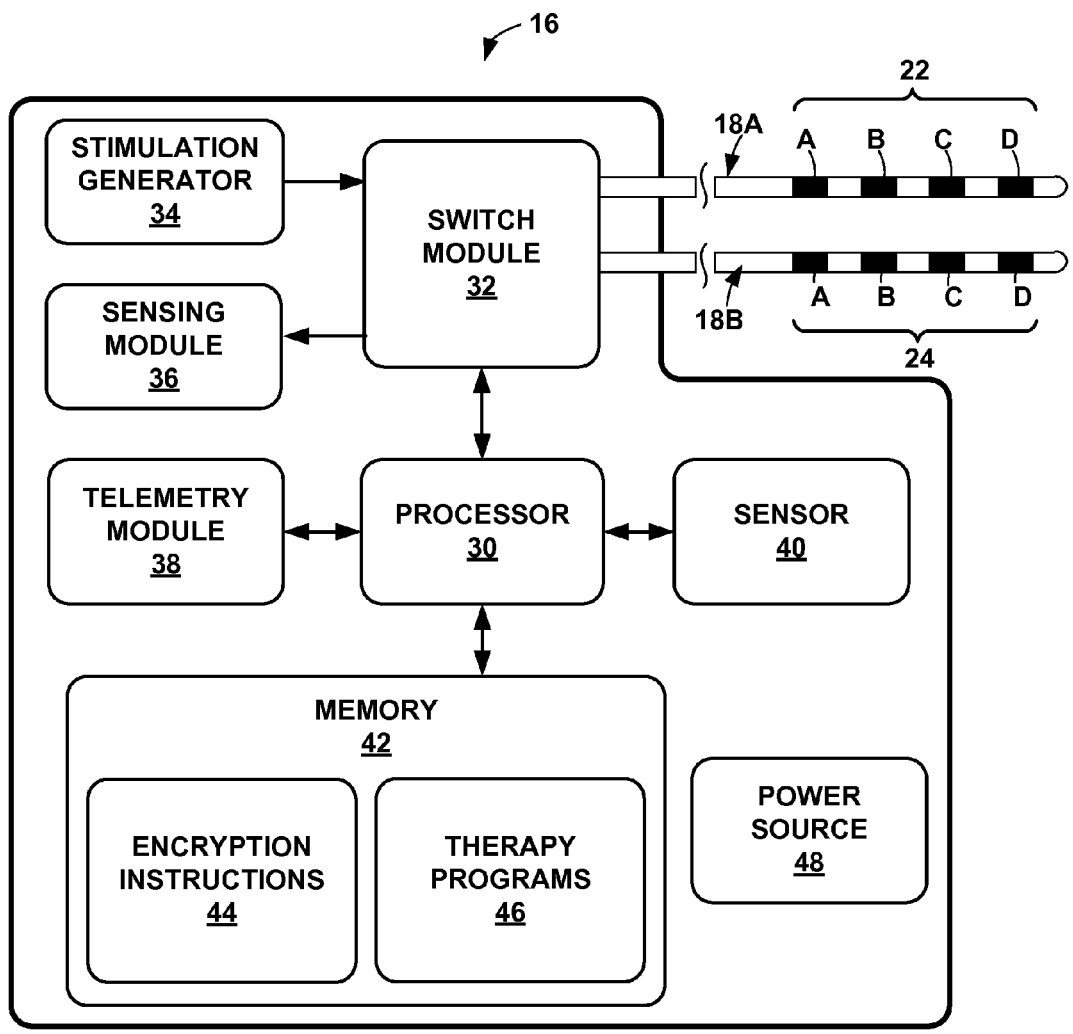
FIG. 2 is a block diagram of the example IMD of FIG. 1 for delivering electrical stimulation therapy and generating encryption keys.

FIG. 2 is a block diagram of example IMD 16 of FIG. 1 for delivering electrical stimulation therapy and generating encryption keys. IMD 16 may be configured to provide and control SCS therapy. In the example shown in FIG. 2, IMD 16 includes processor 30, memory 42, stimulation generator 34, sensing module 36, switch module 32, telemetry module 38, sensor 40, and power source 48. Memory 42 may include any volatile or non-volatile media, such as a random access memory (RAM), read only memory (ROM), non-volatile RAM (NVRAM), electrically erasable programmable ROM (EEPROM), flash memory, and the like. Memory 42 may store computer-readable instructions that, when executed by processor 30, cause IMD 16 to perform various functions, such as delivering stimulation therapy and generating encryption keys. Memory 42 may be a storage device or other non-transitory medium.

In the example shown in FIG. 2, memory 42 stores, among other data, therapy programs 46 and encryption instructions 44 in separate memories within memory 42 or separate areas within memory 42. In some cases, encryption instructions 44 and/or any encryption keys may be firewalled from various components, such as telemetry module 38, to reduce the likelihood of an unauthorized user from obtaining encryption keys or other encryption information. Each stored therapy program 46 defines a particular set of electrical stimulation parameters (e.g., a therapy parameter set) and corresponding parameter values, such as a stimulation electrode combination, electrode polarity, current or voltage amplitude, pulse width, and pulse rate. In some examples, individual therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Encryption instructions 44 may include instructions that cause processor 30 and/or another processor (e.g., a dedicated encryption module configured to perform encryption tasks described herein) to generate encryption keys using movement information from sensor 40. These instructions may include commands for operating and/or retrieving data from sensor 40, instructions or algorithms for determining sets of values representative of one or more characteristics of the movement information, and generating encryption keys using a determined set of values. IMD 16 may receive encryption instructions 44 during manufacture or otherwise prior to being implanted in patient 12 to maintain security of the encryption instructions. In some examples, IMD 16 may receive updates to encryption instructions 44 after IMD 14 has been implanted in patient 12.

Stimulation generator 34, under the control of processor 30, is configured to generate stimulation signals for delivery to patient 12 via selected combinations of electrodes 22, 24. Lead 18A includes electrodes 22A, 22B, 22C, and 22D (collectively "electrodes 22). Lead 18B includes electrodes 24A, 24B, 24C, and 24D (collectively "electrodes 24"). Leads 18 may include fewer or greater than four electrodes each. Accordingly, in some examples, stimulation generator 34 generates electrical stimulation signals in accordance with various electrical stimulation parameters appropriate for SCS or some other therapy selected to treat one or more conditions of patient 12. Therapy programs, therapy parameter values, and other instructions that define therapy delivery may be selected by the clinician, patient 12, and/or updated over time. While stimulation pulses are generally described, stimulation signals may be of any form, such as continuous-time signals (e.g., sine waves) or the like.

Processor 30 may include any one or more of a microprocessor, a controller, a digital signal processor (DSP), an application specific integrated circuit (ASIC), a field-programmable gate array (FPGA), discrete logic circuitry, and the functions attributed to processor 30 herein may be embodied as firmware, hardware, software or any combination thereof. Processor 30 controls stimulation generator 34 according to therapy programs 46 stored in memory 42 to apply particular stimulation parameter values specified by one or more of programs, such as amplitude, pulse width, and pulse rate.

In the example shown in FIG. 2, the set of electrodes 22 and 24 can be used to deliver electrical stimulation to patient 12. Processor 30 also controls switch module 32 to apply the stimulation signals generated by stimulation generator 34 to selected combinations of electrodes 22, 24. In particular, switch module 32 may couple stimulation signals to selected conductors within leads 18, which, in turn, deliver the stimulation signals across selected electrodes 22, 24. Switch module 32 may be a switch array, switch matrix, multiplexer, or any other type of switching module configured to selectively couple stimulation energy to selected electrodes 22, 24. Hence, stimulation generator 34 is coupled to electrodes 22, 24 via switch module 32 and conductors within leads 18. In some examples, however, IMD 16 does not include switch module 32.

Stimulation generator 34 may be a single channel or multi-channel stimulation generator. In particular, stimulation generator 34 may be capable of delivering a single stimulation pulse, multiple stimulation pulses, or a continuous signal at a given time via a single electrode combination or multiple stimulation pulses at a given time via multiple electrode combinations. Although sensing module 36 is incorporated into a common housing with stimulation generator 34 and processor 30 in FIG. 2, in other examples, sensing module 36 may be in a separate housing from IMD 16 and may communicate with processor 30 via wired or wireless communication techniques.

Sensor 40 may include one or more sensing elements that sense or detect motion of IMD 16. Sensor 40 may then generate and output movement information for use by processor 30 to identify patient activity and generate encryption keys from a bump session with another device (e.g., programmer 20). For example, sensor 40 may include one or more accelerometers (e.g., single axis, two axis, or three-axis accelerometers), gyroscopes, optical sensors, pressure sensors, mercury switches, or any other types of sensors configured to detect motion. Sensor 40 may output the movement information as one or more analog signals, digital data streams, or other type of information interpretable by one or more components. For example, processor 30 may determine sets of values representative of one or more characteristics of the movement information and/or generate encryption keys using the sets of values. Although sensor 40 may be contained within a housing of IMD 16, a remote sensor 40 may be used in other examples. For example, a sensor may be implanted remote from IMD 16 such that sensor 40 is close to the skin of patient 16 and better located to detect bumps from programmer 20 during a bump session. The remote sensor may then transmit movement information indicative of the detected motion via a wired lead or wireless signals to IMD 16.

Telemetry module 38 supports wireless communication between IMD 16 and external programmer 20 or another computing device under the control of processor 30. Processor 30 of IMD 16 may receive, as updates to programs, values for various stimulation parameters such as amplitude and electrode combination, from programmer 20 via telemetry module 38. Some or all of these communications from programmer 20 may be encrypted using an encryption key generated by programmer 20 based on the detected motion during the bump session and matching the encryption key generated by IMD 16. The updates to the therapy programs may be stored within therapy programs 46 portion of memory 42. IMD 16 may also transmit, via telemetry module 38, encrypted information (e.g., sensed patient data or operational information of IMD 16) to programmer 20. Telemetry module 38 in IMD 16, as well as telemetry modules in other devices and systems described herein, such as programmer 20, may accomplish communication by radiofrequency (RF) communication techniques. In addition, telemetry module 38 may communicate with external medical device programmer 20 via proximal inductive interaction of IMD 16 with programmer 20. Accordingly, telemetry module 38 may send information to external programmer 20 on a continuous basis, at periodic intervals, or upon request from IMD 16 or programmer 20.

Power source 48 delivers operating power to various components of IMD 16. Power source 48 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Figure 3:
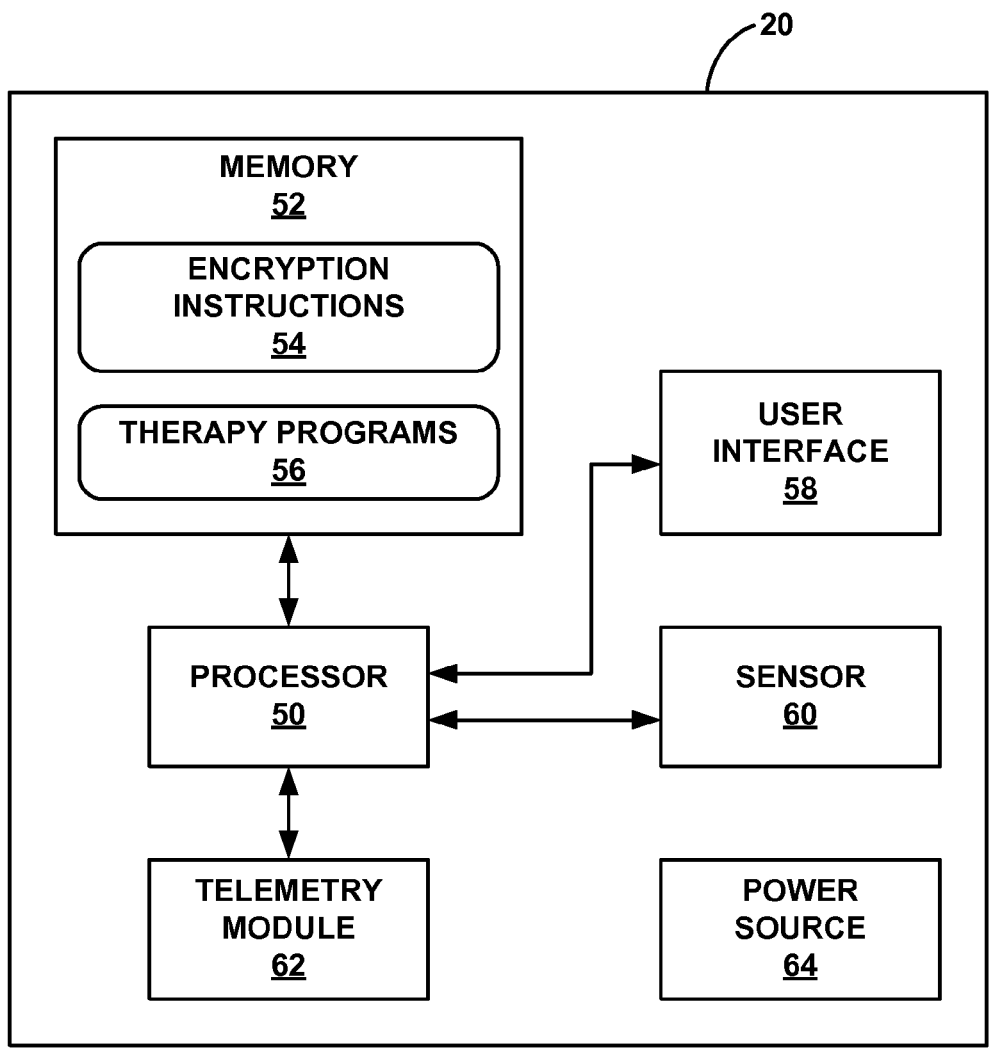
FIG. 3 is a block diagram of the external programmer of FIG. 1.

FIG. 3 is a block diagram of external programmer 20 of FIG. 1. Although programmer 20 may generally be described as a hand-held device, programmer 20 may be a larger portable device or a more stationary device. In addition, in other examples, programmer 20 may be included as part of an external charging device or include the functionality of an external charging device. As illustrated in FIG. 3, programmer 20 may include a processor 50, memory 52, user interface 58, sensor 60, telemetry module 62, and power source 64. Memory 52 may store instructions that, when executed by processor 50, cause processor 50 and external programmer 20 to provide the functionality ascribed to external programmer 20 throughout this disclosure.

In general, programmer 20 comprises any suitable arrangement of hardware, alone or in combination with software and/or firmware, to perform the techniques attributed to programmer 20, and processor 50, user interface 58, and telemetry module 62 of programmer 20. In various examples, programmer 20 may include one or more processors, such as one or more microprocessors, DSPs, ASICs, FPGAs, or any other equivalent integrated or discrete logic circuitry, as well as any combinations of such components. Programmer 20 also, in various examples, may include a memory 52, such as RAM, ROM, PROM, EPROM, EEPROM, flash memory, a hard disk, a CD-ROM, comprising executable instructions for causing the one or more processors to perform the actions attributed to them. Moreover, although processor 50 and telemetry module 62 are described as separate modules, in some examples, processor 50 and telemetry module 62 are functionally integrated. In some examples, processor 50 and telemetry module 62 correspond to individual hardware units, such as ASICs, DSPs, FPGAs, or other hardware units.

Memory 52 (e.g., a storage device) may store instructions that, when executed by processor 50, cause processor 50 and programmer 20 to provide the functionality ascribed to programmer 20 throughout this disclosure. For example memory 52 may include instructions that cause processor 50 to obtain a parameter set from memory, receive a user input and send a corresponding command to IMD 16, generate encryption keys, or any other functionality. In addition, memory 52 may include a plurality of therapy programs, where each program includes a parameter set that defines stimulation therapy.

In the example shown in FIG. 3, memory 52 stores, among other data, therapy programs 56 and encryption instructions 54 in separate memories within memory 52, separate areas within memory 52, or even the same area of memory 52 In some cases, encryption instructions 54 and/or any encryption keys may be firewalled from various components, such as telemetry module 62, to reduce the likelihood of an unauthorized user from obtaining encryption keys or other encryption information. Each stored therapy program 56 defines a particular set of electrical stimulation parameters (e.g., a therapy parameter set) and corresponding parameter values, such as a stimulation electrode combination, electrode polarity, current or voltage amplitude, pulse width, and pulse rate. In some examples, individual therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis. One or more of therapy programs 56 may be transmitted to IMD 16 via encrypted communication.

Similar to encryption instructions 44 of IMD 16, encryption instructions 54 may include instructions that cause processor 50 and/or another processor (e.g., a dedicated encryption module configured to perform encryption tasks described herein) to generate encryption keys using movement information from sensor 60. These instructions may include commands for operating and/or retrieving data from sensor 60, instructions for determining sets of values representative of one or more characteristics of the movement information, and instructions for generating encryption keys using a determined set of values. Instructions may include one or more algorithms in some examples. Programmer 20 may receive encryption instructions 54 during manufacture or during another secure environment. In some examples, programmer 20 may receive updates to encryption instructions 54 via a wired connection with another device to reduce unauthenticated access to the instructions.

Encryption instructions 54 may also vary depending upon whether programmer 20 is configured as a clinician programmer or a patient programmer. For example, the expiration of generated encryption keys may depend upon whether programmer 20 is intended for clinician or patient use. In patient use, encryption keys programmer 20 and IMD 16 may remain valid for a long periods of time (e.g., months or years) or even never expire. In contrast, programmer 20 configured for clinician use may require more frequent generation of encryption keys to maintain security. For example, a generated encryption key for a clinician programmer may remain valid for only several hours or days (e.g., 8 hours, 16 hours, or 24 hours). This may allow the clinician device to communicate with IMD 16 for the duration of a clinic visit by patient 12, for example. After an encryption key expires, a new encryption key may be generated after performing a new bump session between programmer 20 and IMD 16.

Sensor 60 may be similar to sensor 40 of IMD 16. Sensor 60 may include one or more sensing elements that sense or detect motion of programmer 20. Sensor 60 may then generate and output movement information for use by processor 50 to identify motion of the programmer and generate encryption keys from a bump session with another device (e.g., one or more IMDs such as IMD 16). For example, sensor 60 may include one or more accelerometers (e.g., single-axis, two-axis, or three-axis accelerometers), gyroscopes, optical sensors, pressure sensors, mercury switches, or any other types of sensors configured to detect motion. Sensor 60 may output the movement information as one or more analog signals, digital data streams, or other type of information interpretable by one or more components. For example, processor 50 may determine sets of values representative of one or more characteristics of the movement information and/or generate encryption keys using the sets of values. Although sensor 60 may be contained within a housing of programmer 20, a remote sensor 60 may be housed within a dongle or other housing that is designed to be bumped with an IMD. The remote sensor may then transmit movement information indicative of the detected motion via a wired connection or wireless signals to programmer 20.

User interface 58 may include a button or keypad, lights, a speaker for voice commands, a display device, such as a liquid crystal (LCD), light-emitting diode (LED), or organic light-emitting diode (OLED). In some examples the display device may be a touch screen (e.g., a presence-sensitive screen). User interface 58 may be configured to display any information related to the delivery of stimulation therapy, identified patient behaviors, sensed patient parameter values, patient behavior criteria, or any other such information. User Interface 58 may also be configured to display instructions related to a bump session, such as when and how to bump programmer 20 with IMD 16. User interface 58 may also receive user input. The input may be, for example, in the form of pressing a button on a keypad or selecting an icon from a touch screen. The input may be a request to initiate communication with IMD 16, which may cause programmer 20 to initiate a bump session and generation of encryption keys.

Telemetry module 62 may support wireless communication between IMD 16 and programmer 20 under the control of processor 50. Telemetry module 62 may also be configured to communicate with another computing device via wireless communication techniques, or direct communication through a wired connection. In some examples, telemetry module 62 may be substantially similar to telemetry module 38 of IMD 16 described herein, providing wireless communication via an RF or proximal inductive medium. In some examples, telemetry module 62 may include an antenna, which may take on a variety of forms, such as an internal or external antenna.

Processor 50 of programmer 20 may receive patient data from IMD 16 and/or transmit updates for values for various therapy parameters such as amplitude and electrode combination via telemetry module 62. Some or all of these communications from programmer 20 may be encrypted using an encryption key generated by programmer 20 based on the detected motion during the bump session and matching the encryption key generated by IMD 16. Programmer 20 may also transmit, via telemetry module 62, encrypted information (e.g., one of therapy programs 56 or adjustments to therapy parameter values) to IMD 16.

Examples of local wireless communication techniques that may be employed to facilitate communication between programmer 20 and IMD 16 include RF communication according to the 802.11 or Bluetooth specification sets or other standard or proprietary telemetry protocols. In this manner, other external devices may be capable of communicating with programmer 20 without needing to establish a secure wireless connection. As described herein, telemetry module 62 may be configured to transmit a spatial electrode movement pattern or other stimulation parameter values to IMD 16 for delivery of stimulation therapy.

Figure 4:
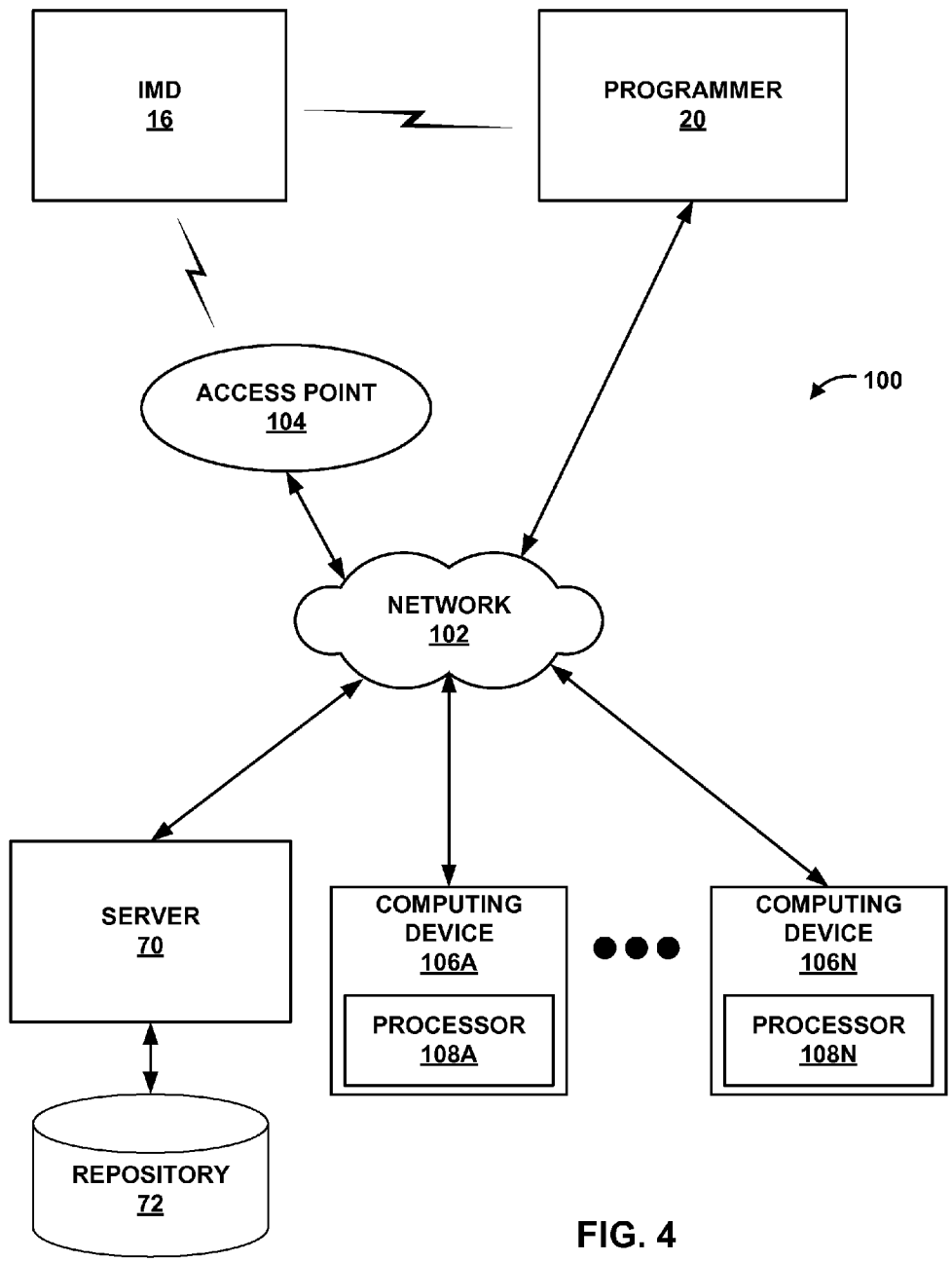
FIG. 4 is a block diagram illustrating an example system that includes a networked server coupled to an IMD and one or more computing devices via a network.

FIG. 4 is a block diagram illustrating an example system 100 that includes a networked server coupled to IMD 16 and one or more computing devices via network 102. As shown in FIG. 4, server 70 (e.g., a networked external computing device) and one or more computing devices 106A-106N (collectively "computing devices 106") that are coupled to the IMD 16 and programmer 20 shown in FIG. 1 via a network 102. Network 102 can be generally used to transmit therapy programs, therapy parameter adjustments, sensed patient data, or any other information between IMD 16, programmer 20, server 70 and/or computing devices 106.

In some examples, IMD 16 and/or programmer 20 may transmit movement information from a bump session to server 70 and/or computing devices 106 for processing and determination of the set of values indicative of the one or more characteristics of the detected motion. Processing the movement information may be computationally intensive and require power. Offloading this task to server 70, for example, may provide for faster determination (e.g., calculation) of the set of values and prevent excess drain of battery power from programmer 20 and/or IMD 16. Once server 70 determines the set of values, server 70 may transmit the set of values back to programmer 20 and/or IMD 16. Each of programmer 20 and IMD 16 independently generate the encryption key using the received set of values to avoid transmission of the encryption keys.

In other examples, the information transmitted by IMD 16 may allow a clinician or other healthcare professional to monitor patient 12 remotely. In some examples, IMD 16 may use a telemetry module to communicate with programmer 20 via a first wireless connection, and to communicate with access point 104 via a second wireless connection, e.g., at different times. In the example of FIG. 4, access point 104, programmer 20, server 70 and computing devices 106 are interconnected, and able to communicate with each other through network 102. In some cases, one or more of access point 104, programmer 20, server 70 and computing devices 106 may be coupled to network 102 via one or more wireless connections. IMD 16, programmer 20, server 70, and computing devices 106 may each comprise one or more processors, such as one or more microprocessors, DSPs, ASICs, FPGAs, programmable logic circuitry, or the like, that may perform various functions and operations, such as those described herein. Computing devices 106 may include respective processors 108.

Access point 104 may comprise a device that connects to network 102 via any of a variety of connections, such as telephone dial-up, digital subscriber line (DSL), or cable modem connections. In other examples, access point 104 may be coupled to network 102 through different forms of connections, including wired or wireless connections. In some examples, access point 104 may be co-located with patient 12 and may comprise one or more programming units and/or computing devices (e.g., one or more monitoring units) that may perform various functions and operations described herein. For example, access point 104 may include a home-monitoring unit that is co-located with patient 12 and that may monitor the activity of IMD 16. In some examples, server 70 or computing devices 106 may control or perform any of the various functions or operations described herein.

In some cases, server 70 may be configured to provide a secure storage site (e.g., via repository 72) for therapy parameters, patient parameters, sensed data, or other data that has been collected and generated from IMD 16 and/or programmer 20. Network 102 may comprise a local area network, wide area network, or global network, such as the Internet. The system of FIG. 4 may be implemented, in some aspects, with general network technology and functionality similar to that provided by the Medtronic CareLink® Network developed by Medtronic, Inc., of Minneapolis, Minn.

Figure 5:
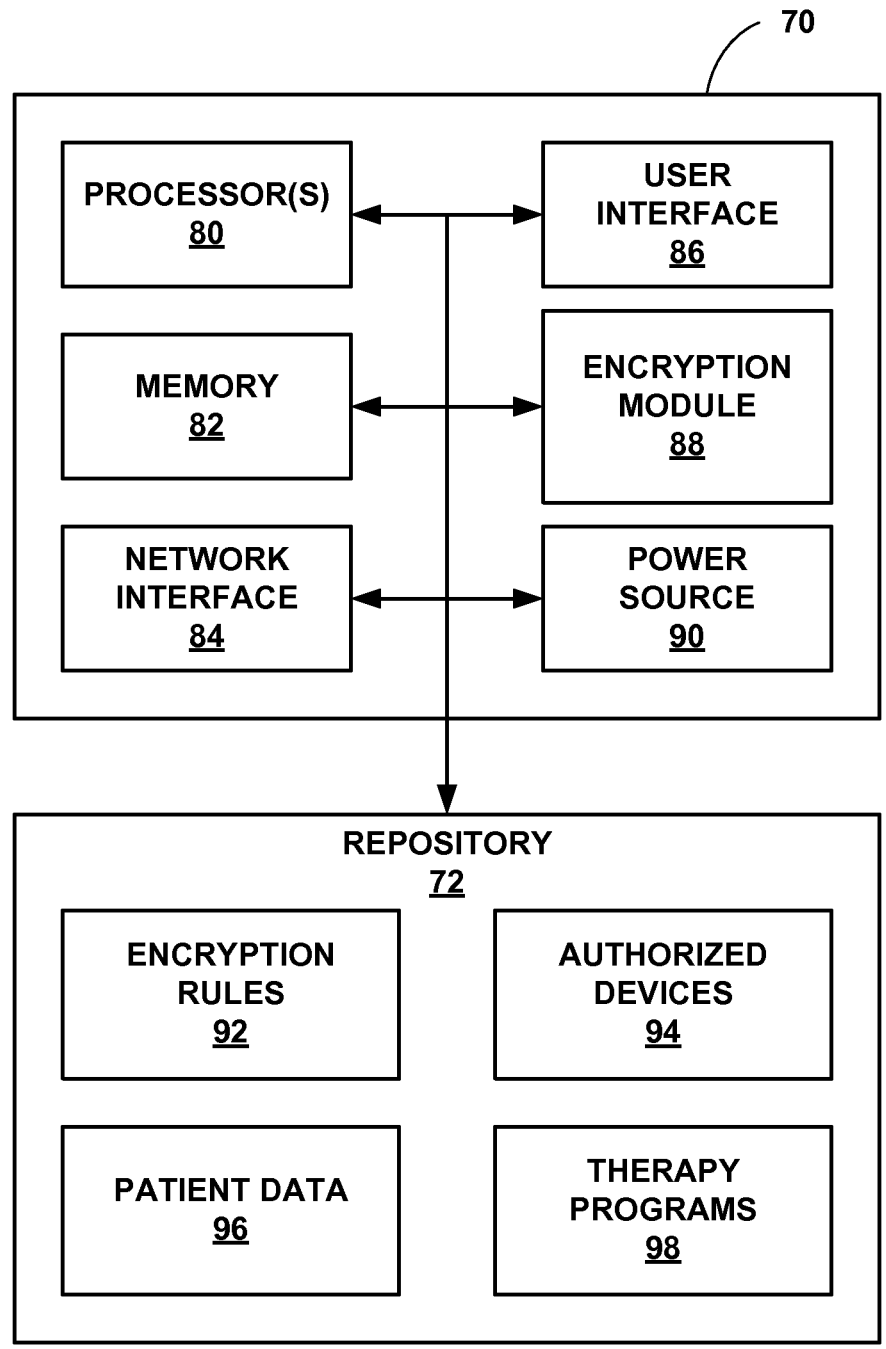
FIG. 5 is a block diagram of the networked server of FIG. 4.

FIG. 5 is a block diagram of networked server 70 and repository 72 of FIG. 4. FIG. 5 illustrates only one particular example of server 70, and many other example embodiments of server 70 may be used in other instances. For example, server 70 may include additional components and run multiple different applications. Server 70 may be configured to perform various tasks related to delivering patient therapy, distributing data amongst different computing devices, facilitate remote patient monitoring and therapy control, and any other such features. In addition, server 70 may facilitate the creation of encryption keys based on detected motion during a bump session between two devices, e.g., programmer 20 and IMD 16. For example, performing the calculations necessary for determining a set of values representative of the movement information may be computationally intensive. Therefore, programmer 20 or IMD 16 may preserve computational resources and reduce power usage by offloading these tasks to server 70.

As shown in the specific example of FIG. 5, server 70 may include and/or house one or more processors 80, memory 82, a network interface 84, user interface 86, encryption module 88, and power source 90. Server 70 may be in communication with repository 72, such that repository 72 is located external of server 70. In other examples, repository 72 may include one or more storage devices within an enclosure of server 70. Server 70 may also include an operating system, which may include modules and/or applications that are executable by processors 80 and server 70. Each of components 80, 82, 84, 86, 88, and 90 may be interconnected (physically, communicatively, and/or operatively) for inter-component communications.

Processors 80, in one example, are configured to implement functionality and/or process instructions for execution within server 70, such as analyzing patient data and distributing data to other devices. For example, processors 80 may be capable of processing instructions stored in memory 82 or instructions stored in repository 72. These instructions may define or otherwise control the operation of server 70.

Memory 82, in one example, is configured to store information within server 70 during operation. Memory 82, in some examples, is described as a computer-readable storage medium. Memory 82 may also be described as a storage device or computer-readable storage device. In some examples, memory 82 is a temporary memory, meaning that a primary purpose of memory 82 is not long-term storage. However, memory 82 may also be described as non-transitory. Memory 82, in some examples, may be described as a volatile memory, meaning that memory 82 does not maintain stored contents when the computer is turned off. Examples of volatile memories include random access memories (RAM), dynamic random access memories (DRAM), static random access memories (SRAM), and other forms of volatile memories known in the art. In some examples, memory 82 is used to store program instructions for execution by processors 80. Memory 82, in one example, is used by software or applications running on server 70 to temporarily store information during program execution. Although memory 82 of FIG. 5 is not described as including encryption rules 92, memory 82 may store such data in other examples.

Repository 72, in some examples, also includes one or more computer-readable storage media, such as one or more storage devices. Repository 72 may be a non-transitory medium. Repository 72 may be configured to store larger amounts of information than memory 82. Repository 72 may further be configured for long-term storage of information. In some examples, repository 72 may include non-volatile data storage elements. Examples of such non-volatile storage elements include magnetic hard discs, optical discs, floppy discs, flash memories, or forms of electrically programmable memories (EPROM) or electrically erasable and programmable (EEPROM) memories.

Repository 72 may be configured to store a variety of information. For example, repository 72 may store encryption rules 92 that includes instructions and information related to generation of encryption keys. Encryption rules 92 may include instructions regarding how to determine sets of values representing one or more characteristics of movement information from a bump session. These instructions or algorithms may include instructions for generation of amplitude thresholds, time durations between acceleration changes, frequency information, or any other characteristics that encryption module 88 may use to characterize the movement information. Encryption rules 92 may include some or all of the same instructions stored by programmer 20 and/or IMD 16.

Repository 72 may also include additional data related to the monitoring and/or treatment of one or more patients. For example, repository 72 may include lists of authorized devices 94 (e.g., medical devices, monitoring equipment, and programming devices). Repository 72 may also include patient data 96 and therapy programs 98 for one or more patients.

In some examples, encryption module 88 (which may include one or more dedicated processors) may be configured to receive movement information from programmer 20 and/or IMD 16 and determine the set of values used by programmer 20 or IMD 16 to generate encryption keys. Encryption module 88 may retrieve algorithms, rules, or other instructions from encryption rules 92 of repository 72 to determine the appropriate set of values representative of one or more characteristics of the movement information from the bump session. Encryption module 88 may then determine a set of values for programmer 20 or IMD 16 and transmit the set of values back to the respective device for independent generation of an encryption key. In this manner, encryption module 88 may be used to generate the set of values when such generation is computationally intensive or otherwise benefitted from server 70 performing the calculations.

Server 70, in some examples, also includes a network interface 84. Server 70, in one example, utilizes network interface 84 to communicate with other computing devices (e.g., computing device 106), programmers (e.g., programmer 20 of FIG. 3), medical devices, or more networks, such as network 102 shown in FIG. 4. Network interface 84 may be a network interface card, such as an Ethernet card or other wired interface. In other examples, network interface 84 may include an optical transceiver, a radio frequency transceiver, or any other type of device that can send and receive information. Other examples of such network interfaces may include Bluetooth, 3G and WiFi radios in mobile computing devices as well as USB. In some examples, server 70 utilizes network interface 84 to wirelessly communicate with another computing device or other networked computing devices.

Server 70 in one example, also includes one or more user interfaces 86. User interface 86 may include a touch-sensitive and/or a presence-sensitive screen, mouse, a keyboard, a voice responsive system, camera, or any other type of device for detecting a command from a user. In one example, user interface 86 may include a touch-sensitive screen, sound card, a video graphics adapter card, or any other type of device for converting a signal into an appropriate form understandable to humans or machines. In addition, user interface 86 may include a speaker, a cathode ray tube (CRT) monitor, a liquid crystal display (LCD), or any other type of device that can generate intelligible output to a user.

Server 70, in some examples, includes one or more power sources 90, which provide power to server 70. Generally, power source 90 may utilize power obtained from a wall receptacle or other alternating current source. However, in other examples, power source 90, may include one or more rechargeable or non-rechargeable batteries (e.g., constructed from nickel-cadmium, lithium-ion, or other suitable material). In other examples, power source 90 may be a power source capable of providing stored power or voltage from another power source.

FIGS. 6-8 illustrate example techniques for generating encryption keys from detected motion. Each of FIGS. 6-8 will be described with respect to IMD 16, but programmer 20 may also be configured to perform similar operations in order for both programmer 20 and IMD 16 to have matching encryption keys resulting from being bumped together. The magnitudes of acceleration are shown in G's (or a normalized acceleration with respect to acceleration due to gravity), but the acceleration could be represented as other units or even as voltages or other signals representative of such acceleration. As described herein, each of IMD 16 and programmer 20 may generate the same set of values, and encryption key, from the sensed acceleration at each device. The algorithms used to generate the set of values may be coarse enough to generate the same set of values even though each of IMD 16 and programmer 20 may sense a different magnitude and/or frequency of the accelerations. In some examples, IMD 16 and/or programmer 20 may calibrate the acceleration signals to achieve more uniform data from which the set of values are determined. FIG. 6 is a graph illustrating the generation of an example encryption key from detected motion and a single amplitude threshold.

As shown in FIG. 6, graph 110 includes acceleration signal 112. Acceleration signal 112 represents the accelerations detected by sensor 40 of IMD 16 during the bump session with programmer 20. Graph 110 shows the amplitude of acceleration signal 112 with respect to time. Greater amplitudes of acceleration signal 112 represent a greater change in acceleration that may be indicative of a bump event between IMD 16 and programmer 20.

In the example of FIG. 6, determining the set of values used to generate the encryption key includes identifying when supra-threshold amplitude peaks (e.g., acceleration signal 112 is greater than amplitude threshold 114) in acceleration signal 112 occur during the bump session. In this manner, the characteristics indicative of the movement information include the amplitudes of acceleration signal 112 and the timing of the amplitude peaks within bump session. The set of values determined from acceleration signal 112 as shown in graph 110 may thus be representative of the amplitudes of the acceleration detected during the bump session.

Processor 30 of IMD 16 may first segment the bump session into a plurality of time slots 116A-116J (collectively "time slots 116"). Each of time slots 116 may be of a predetermined duration or selected such that the bump session is divided into a predetermined number of time slots. The time slots may also be selected based on the duration of the bump session. For example, the time period of the bump session may be a predetermined amount of time (e.g., 10 seconds) that is divided into equal time slots (e.g., 100 milliseconds for each time slot, resulting in 100 time slots over the 10 second period). In this specific example, the 100 time slots could result in a 100-bit encryption value for the encryption key. Therefore, the number of time slots 116 may be selected to achieve an encryption value of a desired size (e.g., 8-bit, 40-bit, 64-bit, 128-bit, etc.). Alternatively, processor 30 may select a subset of the time slots to achieve the desired encryption value or further process the set of values to achieve the desired encryption value. Each of the time slots may have a duration generally between 10 milliseconds and 5 seconds. Time slot durations less than one second may be preferred in some examples. In some examples, the number of time slots 116 may be determined to achieve a variation in the set of values (e.g., not all of the values in the set are the same). In this manner, instructions for determining the set of values may include instructions for defining the time slots such that a variation in the set of values occurs. The time slots may this be defined at the start in this manner or re-defined in response to an error in which the set of values includes all of the same values (e.g., all zeros). Alternatively, processor 30 may prompt the user to provide additional bumps between programmer 20 and IMD 14.

For each of the plurality of time slots 116, processor 30 may compare the amplitude of acceleration signal 112 of the movement information to amplitude threshold 114. Amplitude threshold 114 may be set to a predetermined threshold above which acceleration signal 112 is indicative of a bump between programmer 20 and IMD 16. In other examples, amplitude threshold 114 may be determined based on a minimum amplitude value of signal 112, an average amplitude of signal 112, or a maximum value of signal 112. As shown in the example of FIG. 6, amplitude threshold 114 is set to approximately 0.4 G's.

Processor 30 may then assign first and second values to the appropriate time slots 116 based on when the amplitude of acceleration signal 112 exceeds amplitude threshold 114. The first and second values may be a binary code using 0's and 1's, for example. Processor 30 may assign the first value to each of time slots 116 in which the amplitude of acceleration signal 112 exceeds amplitude threshold 114. As shown in the example of FIG. 6, time slots 116C, 116F, 116G, and 116I would be assigned a 1 because supra-threshold amplitudes occurred during these time slots. Accordingly, processor 30 may assign a second value to each of time slots 116 in which the amplitude of acceleration signal 112 does not exceed amplitude threshold 114. As shown in the example of FIG. 6, time slots 116A, 116B, 116D, 116E, 116H, and 116J would be assigned a 0 because acceleration signal 112 remained sub-threshold during these time slots. Processor 30 may then be configured to order the first and second values according to a chronological sequence of time slots 116 to create the set of values. In the example of FIG. 6, the resulting set of values would be "0010011010." This set of values is merely one example. In other examples, processor 30 may generate larger sets of values from smaller time slots, alternative thresholds, a greater number of bumps, etc.

This determined set of values may then be used by processor 30 of IMD 16 as the encryption key. In other words, processor 30 may generate the encryption key as the set of values. In the example of FIG. 6, the set of values would equate to a 10-bit encryption value. In other examples, processor 30 may apply one or more additional algorithms to the set of values in order to generate the encryption key. For example, processor 30 may apply a multiplication factor, add values to the beginning, middle, or end of the set of values, subtract values from the beginning, middle, or end of the set of values, or otherwise change the set of values. The modification of the set of values may be performed to format the set of values into a desired encryption key or augment the set of values to further reduce the likelihood of an unauthorized user obtaining the encryption key by monitoring the bump session.

FIG. 7 is a graph illustrating the generation of an example encryption key from detected motion and multiple amplitude thresholds. As shown in FIG. 7, graph 120 includes acceleration signal 122. Acceleration signal 122 represents the accelerations detected by sensor 40 of IMD 16 during the bump session with programmer 20. Graph 120 shows the amplitude of acceleration signal 122 with respect to time. Greater amplitudes of acceleration signal 122 represent a greater change in acceleration that may be indicative of a bump event between IMD 16 and programmer 20.

In the example of FIG. 7, determining the set of values used to generate the encryption key includes identifying the magnitude of amplitude peaks (e.g., acceleration signal 122 is greater than one or more different amplitude thresholds) in acceleration signal 122 occur during the bump session. In this manner, the characteristics indicative of the movement information include the amplitudes of acceleration signal 122 within bump session. The set of values determined from acceleration signal 122 as shown in graph 120 may thus be representative of the magnitudes of different amplitude peaks of the acceleration detected during the bump session. Multiple amplitude thresholds 124A, 124B, 124C, and 124D (collectively "amplitude thresholds 124") may be used to determine the set of values from the magnitude of amplitude peaks within acceleration signal 122.

Processor 30 of IMD 16 may compare the amplitude of acceleration signal 122 of the movement information to amplitude thresholds 124. Each of amplitude thresholds 124 may be set to identify different magnitudes of accelerations representative of the varying force with which each bump between IMD 16 and programmer 20 occurred during the bump session. The amplitudes thresholds 124 may be determined based on a minimum amplitude value of signal 122, an average amplitude of signal 122, or a maximum value of signal 122. For example, thresholds 124 may be normalized to the detected amplitudes. As shown in the example of FIG. 7, amplitude thresholds 124A-D are set to approximately 0.2 G's, 0.4 G's, 0.6 G's, and 0.8 G's, respectively. Amplitude thresholds 124 may be equally spaced or separated by different amplitudes. Moreover, the number of amplitude thresholds 124 may vary to include two, three, four, five, or more different amplitude thresholds. A greater number of amplitude thresholds may generate more complex encryption keys, but ensuring that the encryption keys independently generated by IMD 16 and programmer 20 are the same may be more difficult. Each of the plurality of different amplitude thresholds 124 may correspond to a respective value that is used in the set of values (e.g., numerals 0, 1, 2, and 3 as shown in FIG. 7). Alternatively, each peak may be assigned an alphabet letter, value using binary code (e.g., a different set of binary numbers), or other code.

Processor 30 may then assign respective values to each amplitude peak of acceleration signal 122 exceeding at least one threshold. In other words, processor 30 may assign, to each amplitude peak, the value of the highest amplitude threshold exceeded by the peak. In the example, of FIG. 7, amplitude peaks 126A and 126C would be assigned a "3" for exceeding amplitude threshold 124D, amplitude peak 126E would be assigned a "2" for exceeding amplitude threshold 124C but not threshold 124D, amplitude peak 126D would be assigned a "1" for exceeding amplitude threshold 124B but not threshold 124C, and amplitude peaks 126B and 126F would be assigned a "0" for exceeding amplitude threshold 124A but not threshold 124B. Since acceleration signal 122 is only analyzed to generate the set of values based on amplitude peaks, no value may be assigned to any peaks below threshold 124A. Processor 300 may then be configured to order the assigned values according to the chronological occurrence of the respective amplitude peaks 126 during the period of time to create the set of values. In the example of FIG. 7, the resulting set of values would be "303120."

This determined set of values may then be used by processor 30 of IMD 16 as the encryption key. In other words, processor 30 may generate the encryption key as the set of values (e.g., 303120). In other examples, processor 30 may apply one or more additional algorithms to the set of values in order to generate the encryption key. For example, processor 30 may apply a multiplication factor, add values to the beginning, middle, or end of the set of values, subtract values from the beginning, middle, or end of the set of values, or otherwise change the set of values. The modification of the set of values may be performed to format the set of values into a desired encryption key or augment the set of values to further reduce the likelihood of an unauthorized user obtaining the encryption key by monitoring the bump session.

FIG. 8 is a graph illustrating the generation of an example encryption key from durations of time between supra-threshold amplitude peaks of detected motion. As shown in FIG. 8, graph 130 includes acceleration signal 132. Acceleration signal 132 represents the accelerations detected by sensor 40 of IMD 16 during the bump session with programmer 20. Graph 130 shows the amplitude of acceleration signal 132 with respect to time. Greater amplitudes of acceleration signal 132 represent a greater change in acceleration that may be indicative of a bump event between IMD 16 and programmer 20.

In the example of FIG. 8, determining the set of values used to generate the encryption key includes measuring, or calculating, the duration of one or more time periods between respective supra-threshold amplitude peaks of acceleration signal 134 of the movement information generated during the bump session. In this manner, the characteristics indicative of the movement information include the duration of time between amplitude peaks exceeding an amplitude threshold. The set of values determined from acceleration signal 132 as shown in graph 130 may thus be representative of the timing of each detected bump between IMD 16 and programmer 20 during the bump session. In alternative examples, the set of values may be determined by determining the number of intervening time slots between each detected bump.

Processor 30 of IMD 16 may compare the amplitude of acceleration signal 132 of the movement information to amplitude threshold 134. Amplitude threshold 134 may be set to identify amplitude peaks from acceleration signal 132 that are indicative of actual bumps between IMD 16 and programmer 20 as opposed to other motion or noise. Amplitudes threshold 134 may be determined based on a minimum amplitude value of signal 132, an average amplitude of signal 132, or a maximum value of signal 132. For example, threshold 134 may be normalized to the detected amplitudes. As shown in the example of FIG. 8, amplitude threshold 134 is set to approximately 0.2 G's. Processor 30 may identify each of the amplitude peaks exceeding amplitude threshold 134.

Processor 30 may then analyze the time duration between each peak and, in some cases, between the start and end of the bump session and the closest amplitude peak. In other words, processor 30 may generate time markers at the beginning and end of the bump session and at the peak of each time acceleration signal 132 exceeds threshold 134. In other examples, processor 30 may locate the time marker for each peak at the point at which acceleration signal 132 first exceeds amplitude threshold 134 (e.g., on the upslope of each peak). Processor 30 may then calculate the respective time duration between each time marker (i.e., between each pair of amplitude peaks). Time durations 136A-136G (collectively "time durations 136") are shown between each amplitude peak of graph 130. Alternatively, processor 30 may count the number of equidistant time slots between each supra-threshold amplitude peak to determine a value representative of the time duration between each peak.

Processor 30 may then match each of the calculated time durations 136 to one of a plurality of duration ranges. A duration range may be a bucket or category associated with a corresponding value and selected to categorize the calculated time durations 136. Based on the matches, processor 30 may assign values to each of the time durations (or time periods) between each supra-threshold amplitude peak. This assigning may be performed using a look-up table or other data construct. The duration ranges used to categorize each during duration between peaks may vary from two or more duration ranges with different non-overlapping times. In one example, four different duration ranges may be used to categorize durations 136. The duration ranges may include a duration range of less than 100 milliseconds (ms) with a corresponding value of "0," a duration range from 100 ms to 500 ms with a corresponding value of "1," a duration range of 500 ms to 1000 ms with a corresponding value of "2," and a duration range greater than 1000 ms with a corresponding value of "3." These values would then be assigned based on which range the time durations 136 fall into. In the example of FIG. 8, time duration 136C is assigned a "0" for being less than 100 ms, time durations 136B, 136E, and 136G are assigned a "1" for being between 100 ms and 500 ms in duration, time duration 136D is assigned a "2" for being between 500 ms and 1000 ms in duration, and time durations 136A and 136F are assigned a "3" for being greater than 1000 ms. Processor 300 may then be configured to order the assigned values according to the chronological occurrence of the respective time durations during the period of time to create the set of values. In the example of FIG. 8, the resulting set of values would be "3102131."

This determined set of values may then be used by processor 30 of IMD 16 as the encryption key. In other words, processor 30 may generate the encryption key as the set of values (e.g., 3102131). In other examples, processor 30 may apply one or more additional algorithms to the set of values in order to generate the encryption key. For example, processor 30 may apply a multiplication factor, add values to the beginning, middle, or end of the set of values, subtract values from the beginning, middle, or end of the set of values, or otherwise change the set of values. The modification of the set of values may be performed to format the set of values into a desired encryption key or augment the set of values to further reduce the likelihood of an unauthorized user obtaining the encryption key by monitoring the bump session.

In the examples of FIGS. 6-8, an acceleration signal is used to determine the set of values. The acceleration signal may be generated from a single-axis accelerometer or only one direction of a multi-axis accelerometer. Alternatively, the acceleration signal may be a vector produced from a three-axis accelerometer such that the amplitude of the acceleration signal is not sensitive to the direction of each bump between IMD 16 and programmer 20. IMD 16 and programmer 20 may also calibrate sensors 40 and 60 to baseline values immediately prior to initiating the bump session. In addition, sensors 40 and 60, or processors 30 and 50, respectively, may apply one or more filters or signal processing algorithms to isolate the accelerations due to each bump. In some examples, the filtering or processing of the movement information (e.g., the acceleration signal) may be dependent upon the location of IMD 16 within patient 12 to accommodate variables such as nearby internal organs, thickness of tissue between the external surface of the skin and IMD 16, movement of patient 12 during the bumping session, or any other sources of noise or unwanted movement.

Using the sets of values generated from any of the examples of FIGS. 6, 7, and 8, processors 30 and 50 may generate the encryption key. Typically, the encryption key generated by each of processors 30 and 50 may be a symmetric key such that both of IMD 16 and programmer 20 use the same encryption key. To encrypt data, the respective device may use an encryption function (e.g., a cipher function) to apply the encryption key to a set of data. The resulting encrypted data set may be transmitted to another device. When an encrypted message is received by either device, the device may reverse the process and apply the encryption key to decrypt the encrypted data set.

Figure 9:
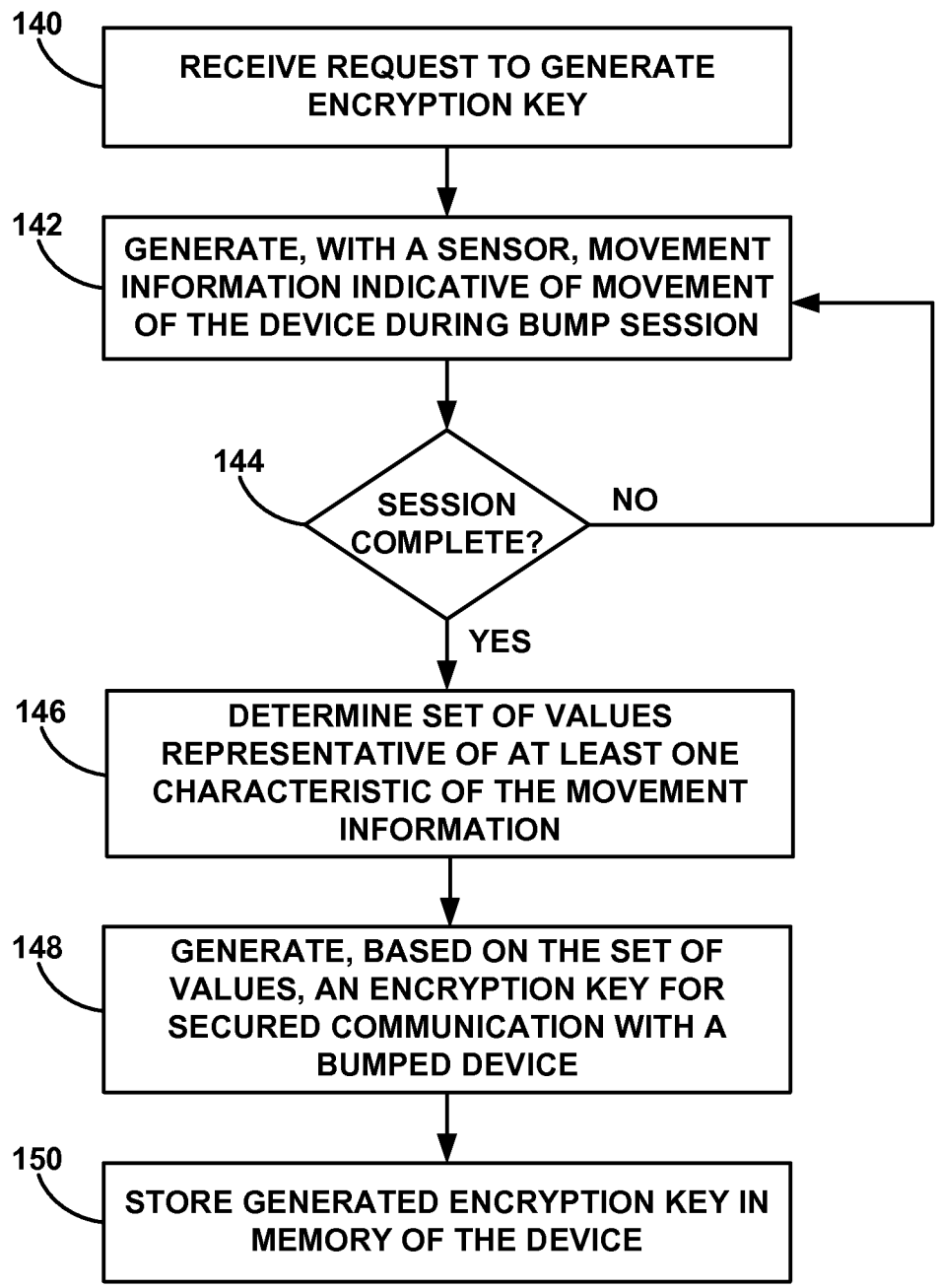
FIG. 9 is a flow diagram illustrating an example process for generating an encryption key from detected motion during a bump session with another device.

FIG. 9 is a flow diagram illustrating an example process for generating an encryption key from detected motion during a bump session with another device. Although FIG. 9 will be described with respect to processor 30 of IMD 16, similar processes would be performed by processor 50 and programmer 20, or the other device with which IMD 16 was bumped to generate matching encryption keys. Other sets of devices may also be used in other examples.

As shown in FIG. 9, processor 30 receives a request to generate an encryption key (140). This request may be in the form of a command (e.g., which may sent unencrypted or using a shared encryption key) from another device (e.g., programmer 20) to generate the key for subsequent communications, an internally generated request when programmer 20 is detected, a request from a user for IMD 16 and programmer 20 to communicate, or any other type of request. In other examples, generation of the encryption key may be initiated when one or both of IMD 16 and programmer 20 senses the presence of each other. One or both of IMD 16 and programmer 20 may include a proximity sensor such as a mechanical switch (detecting physical contact), magnetic field sensor (detection of near-field magnetic signals), or an accelerometer (that detects a tapping or shaking pattern). Upon sensing the presence of another device, IMD 16 may then generate the request for an encryption key usable for secure communications with the sensed device.

In response to receiving the request to generate the encryption key, processor 30 may instruct sensor 40 to generate movement information indicative of movement of IMD 16 during the bump session with programmer 20. IMD 16 and/or programmer 20 may provide instructions to the user (e.g., a clinician or patient) on how and when to move programmer 20 into IMD 16 to perform a "bump." For example, IMD 16 and/or programmer 20 may provide visual, audible, or tactile cues that the bump session has started, when to perform a bump, how many bumps to perform, and/or when the bump session has ended. IMD 16 and/or programmer 20 may provide indications of when a bump is registered by one or both devices, such as an audible tone, flashing light, textual or graphic message, or tactile response (e.g., a vibration). In this manner IMD 16 and/or programmer 20 may provide feedback to the user about the bump session.

If the bump session is not complete ("NO" branch of block 144), processor 30 may continue to control sensor 40 to generate movement information (142). If the bump session is complete ("YES" branch of block 144), processor 30 may determine the set of values that are representative of at least one characteristic of the movement information (146). Example descriptions of determining the set of values are provided in FIGS. 6-8, for purposes of illustration but without limitation as to the techniques described in this disclosure. Therefore, the set of values may be representative of characteristics such as amplitudes, timing, and/or frequency of the movement information. Processor 30 may then generate, based on the set of values, an encryption key for secured communication with the bumped device (e.g., programmer 20) (148). Processor 30 also stores the generated encryption key in memory 42 or other storage device of IMD 16 (150). IMD 16 may then inform programmer 20 that communication can occur or otherwise begin to transmit information, encrypted using the generated encryption key, to programmer 20. In this manner IMD 16 and/or programmer 20 may apply the encryption key to data to generate encrypted data and/or decrypt data by applying the encryption key.

In some examples, IMD 16 and/or programmer 20 may inform the user when secured communication is possible, such as by confirmation that the encryption keys have been successfully generated. In some examples, encryption keys may only be valid for a certain amount of time. Encryption keys may expire after a predetermined amount time elapses (e.g., hours, days, or months), after a predetermined amount of time elapses from the previous communications with the other device, after a predetermined number of communication sessions with the other device, or after one of the devices communicates with a different device.

Since the generation of encryption keys relies upon user bumping of devices together, bumping may result in unacceptable encryption keys (e.g., keys with insufficient entropy). For example, no bump may be registered during a bump session. Since the set of values may be simple without changes to the detected motion, the resulting encryption key might not provide any meaningful encryption. If IMD 16 and/or programmer 20 fail to detect a bump and/or the resulting set of values or encryption key does not meet a minimum entropy value, IMD 16 and/or programmer 20 may restart the process and initiate another bump session. IMD 16 and/or programmer 20 may provide additional instructions to the user in an attempt to obtain more usable movement information and encryption keys with greater entropy.

In some examples the encryption keys themselves may not be used to directly encrypt communications between two devices, such as IMD 16 and programmer 20. Instead, both IMD 16 and programmer 20 may generate session keys from each encryption key. The session keys may be used to secure each communication session. The encryption keys may be referred to as a body area network (BAN) key in some examples to facilitate communications amongst devices related to a patient.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A programmer, such as patient programmer or clinician programmer, or other computing device may also contain a more portable removable memory type to enable easy data transfer or offline data analysis.

The techniques described in this disclosure, including those attributed to IMD 16 and programmer 20, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, remote servers, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. For example, any of the techniques or processes described herein may be performed within one device or at least partially distributed amongst two or more devices, such as between programmer 20, IMD 16, and/or server 70. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described herein. Any combination of the described operations or functions is contemplated. These and other examples are within the scope of the following claims.

What is claimed is:

1. A method comprising:
   receiving, by one of one or more processors of a first device or one or more processors of a networked server, movement information indicative of motion detected by the first device during a period of time in which the first device and a second device were bumped together;
   determining, by one of the one or more processors of the first device or the one or more processors of the networked server, a set of values that represent at least one characteristic of the movement information; and
   generating, by the one or more processors of the first device and based on the set of values, an encryption key for at least one of encrypting or decrypting data communicated between the first device and the second device.

2. The method of claim 1, wherein the at least one characteristic comprises one or more amplitudes of an acceleration signal of the movement information.

3. The method of claim 1, wherein the at least one characteristic comprises one or more time periods between respective supra-threshold amplitude peaks of an acceleration signal of the movement information.

4. The method of claim 1, wherein the characteristic comprises a frequency spectrum of an acceleration signal of the movement information.

5. The method of claim 1, wherein determining the set of values comprises:
   segmenting the period of time into a plurality of time slots;
   for each of the plurality of time slots, comparing an amplitude of an acceleration signal of the movement information to an amplitude threshold;
   assigning a first value to each of the plurality of time slots in which the amplitude of the acceleration signal exceeds the amplitude threshold;
   assigning a second value to each of the plurality of time slots in which the amplitude of the acceleration signal does not exceed the amplitude threshold; and
   ordering the first and second values according to a chronological sequence of the time slots to create the set of values.

6. The method of claim 1, wherein determining the set of values comprises:
   comparing an amplitude of an acceleration signal of the movement information to a plurality of different amplitude thresholds, wherein each of the plurality of different amplitude thresholds corresponds to a respective value;
   for each amplitude peak of the acceleration signal exceeding at least one of the plurality of different amplitude thresholds, assigning, to the amplitude peak, the respective value corresponding to the highest amplitude threshold exceeded by the respective amplitude peak; and
   ordering the assigned values according to the chronological occurrence of the respective amplitude peaks during the period of time to create the set of values.

7. The method of claim 1, wherein determining the set of values comprises:
   comparing an amplitude of an acceleration signal of the movement information to an amplitude threshold;
   for each pair of amplitude peaks of the acceleration signal exceeding the amplitude threshold, calculating a respective time duration between the pair of amplitude peaks;
   matching each of the respective time durations to one of a plurality of duration ranges, wherein each of the plurality of duration ranges corresponds to a respective value;
   assigning, based on the matching, the corresponding value of the matching duration range to the respective time durations; and
   ordering the assigned values according to the chronological occurrence of the respective time durations during the period of time to create the set of values.

8. The method of claim 1, further comprising:
   detecting, by a sensor of the first device, the motion of the first device during the period of time; and
   generating, based on the detection, the movement information.

9. The method of claim 1, further comprising:
   receiving a request to initiate communication between the first device and the second device;
   outputting, for display, a command instructing a user to perform a bump sequence between the first device and the second device, wherein the bump sequence includes one or more physical bumps of the first device against the second device; and
   responsive to receiving the movement information indicative of the bump sequence, determining the set of values.

10. The method of claim 1, wherein the first device is an external medical device programmer and wherein the second device is an implantable medical device.

11. The method of claim 1, further comprising:
applying, by the first device, the encryption key to a set of data to generate an encrypted data set; and
transmitting, by the first device, the encrypted data set to the second device.

12. The method of claim 1, further comprising:
receiving, by the first device, an encrypted data set from the second device; and
applying, by the first device, the encryption key to the encrypted data set to decrypt a set of data.

13. A first device comprising:
one or more processors configured to:
receive movement information indicative of motion detected by the first device during a period of time in which the first device and a second device were bumped together;
determine a set of values that represent at least one characteristic of the movement information; and
generate, based on the set of values, an encryption key for at least one of encrypting or decrypting data communicated between the first device and the second device.

14. The first device of claim 13, wherein the at least one characteristic comprises one or more amplitudes of an acceleration signal of the movement information.

15. The first device of claim 13, wherein the at least one characteristic comprises one or more time periods between respective supra-threshold amplitude peaks of an acceleration signal of the movement information.

16. The first device of claim 13, wherein the characteristic comprises a frequency spectrum of an acceleration signal of the movement information.

17. The first device of claim 13, wherein, to determine the set of values, the one or more processors are configured to:
segment the period of time into a plurality of time slots;
for each of the plurality of time slots, compare an amplitude of an acceleration signal of the movement information to an amplitude threshold;
assign a first value to each of the plurality of time slots in which the amplitude of the acceleration signal exceeds the amplitude threshold;
assign a second value to each of the plurality of time slots in which the amplitude of the acceleration signal does not exceed the amplitude threshold; and
order the first and second values according to a chronological sequence of the time slots to create the set of values.

18. The first device of claim 13, wherein, to determine the set of values, the one or more processors are configured to:
compare an amplitude of an acceleration signal of the movement information to a plurality of different amplitude thresholds, wherein each of the plurality of different amplitude thresholds corresponds to a respective value;
for each amplitude peak of the acceleration signal exceeding at least one of the plurality of different amplitude thresholds, assign, to the amplitude peak, the respective value corresponding to the highest amplitude threshold exceeded by the respective amplitude peak; and
order the assigned values according to the chronological occurrence of the respective amplitude peaks during the period of time to create the set of values.

19. The first device of claim 13, wherein, to determine the set of values, the one or more processors are configured to:

compare an amplitude of an acceleration signal of the movement information to an amplitude threshold;
for each pair of amplitude peaks of the acceleration signal exceeding the amplitude threshold, calculate a respective time duration between the pair of amplitude peaks;
match each of the respective time durations to one of a plurality of duration ranges, wherein each of the plurality of duration ranges corresponds to a respective value;
assign, based on the matching, the corresponding value of the matching duration range to the respective time durations; and
order the assigned values according to the chronological occurrence of the respective time durations during the period of time to create the set of values.

20. The first device of claim 13, further comprising a sensor configured to detect the motion of the first device during the period of time, wherein the one or more processors are configured to generate, based on the detection, the movement information.

21. The first device of claim 13, wherein the one or more processors are configured to:
receive a request to initiate communication between the first device and the second device;
output, for display via a display device, a command instructing a user to perform a bump sequence between the first device and the second device, wherein the bump sequence includes one or more physical bumps of the first device against the second device; and
responsive to receiving the movement information indicative of the bump sequence, determine the set of values.

22. The first device of claim 13, wherein the first device is an external medical device programmer, and wherein the second device is an implantable medical device.

23. The first device of claim 13, wherein the one or more processors are configured to:
apply the encryption key to a set of data to generate an encrypted data set; and
transmit, from the first device, the encrypted data set to the second device.

24. The first device of claim 13, wherein the one or more processors are configured to:
receive an encrypted data set from the second device; and
apply the encryption key to the encrypted data set to decrypt a set of data.

25. A non-transitory computer-readable storage medium comprising instructions that cause one or more processors of a first device to:
receive movement information indicative of motion detected by the first device during a period of time in which the first device and a second device were bumped together;
determine a set of values that represent at least one characteristic of the movement information; and
generate, based on the set of values, an encryption key for at least one of encrypting or decrypting data communicated between the first device and the second device.

26. The non-transitory computer-readable storage medium of claim 25, further comprising instructions that cause the one or more processors of the first device to:
receive a request to initiate communication between the first device and the second device;
output, for display, a command instructing a user to perform a bump sequence between the first device and the second device, wherein the bump sequence includes one or more physical bumps of the first device against the second device; and responsive to receiving the movement information indicative of the bump sequence, determine the set of values.

27. The method of claim 1, further comprising storing the encryption key in a memory of the first device.

28. The method of claim 1, wherein the first device is an implantable medical device, and wherein the second device is an external medical device programmer.

29. The method of claim 1, wherein:
receiving movement information indicative of motion detected by the first device during the period of time in which the first device and the second device were bumped together comprises receiving, by the one or more processors of the networked server, movement information indicative of motion detected by the first device during the period of time in which the first device and the second device were bumped together,
determining the set of values that represent at least one characteristic of the movement information comprises determining, by the one or more processors of the networked server, the set of values that represent at least one characteristic of the movement information, and
wherein the method further comprises transmitting, by the networked server, the set of values to the first device.

30. The method of claim 1, wherein the encryption key is a first encryption key that matches a second encryption key generated by the second device.

31. The first device of claim 13, further comprising a memory configured to store the encryption key.

32. The first device of claim 13, wherein the first device is an implantable medical device, and wherein the second device is an external medical device programmer.

33. The first device of claim 13, wherein the encryption key is a first encryption key that matches a second encryption key generated by the second device.

34. The non-transitory computer-readable storage medium of claim 25, wherein the first device is an external medical device programmer and the second device is an implantable medical device.

35. The non-transitory computer-readable storage medium of claim 25, wherein the first device is an implantable medical device and the second device is an external medical device programmer.

36. A system comprising:
a first device configured to:
generate first movement information indicative of motion detected by the first device during a period of time in which the first device and a second device were bumped together;
determine a first set of values that represent at least one characteristic of the first movement information; and
generate, based on the first set of values, a first encryption key for at least one of encrypting data communicated to the second device or decrypting data received from the second device; and
the second device, wherein the second device is configured to:
generate second movement information indicative of motion detected by the second device during the period of time in which the first device and the second device were bumped together;
determine a second set of values that represent at least one characteristic of the second movement information; and
generate, based on the second set of values, a second encryption key for at least one of encrypting data communicated to the first device or decrypting data received from the first device.

37. The system of claim 36, wherein the first encryption key matches the second encryption key.

38. The system of claim 36, wherein the first device comprises an external medical device programmer, and wherein the second device comprises an implantable medical device.

* * * * *